(12) United States Patent
Jeon et al.

(10) Patent No.: US 9,753,543 B2
(45) Date of Patent: Sep. 5, 2017

(54) TERMINAL AND CONTROL METHOD THEREOF

(71) Applicant: LG ELECTRONICS INC., Seoul (KR)

(72) Inventors: Taeyoung Jeon, Seoul (KR); Raehoon Kang, Seoul (KR); Inyong Hwang, Seoul (KR); Seungbum Hong, Seoul (KR); Seungjin Jang, Seoul (KR); Sungwoo Kim, Seoul (KR); Gyuseog Hong, Seoul (KR)

(73) Assignee: LG ELECTRONICS INC., Seoul (KR)

( * ) Notice: Subject to any disclaimer, the term of this patent is extended or adjusted under 35 U.S.C. 154(b) by 50 days.

(21) Appl. No.: 13/950,158

(22) Filed: Jul. 24, 2013

(65) Prior Publication Data

US 2014/0028546 A1 Jan. 30, 2014

(30) Foreign Application Priority Data

Jul. 27, 2012 (KR) .................. 10-2012-0082721
Mar. 15, 2013 (KR) .................. 10-2013-0028204

(51) Int. Cl.
*G06F 3/01* (2006.01)
*A61B 5/00* (2006.01)
(Continued)

(52) U.S. Cl.
CPC ............... *G06F 3/017* (2013.01); *A61B 5/11* (2013.01); *A61B 5/681* (2013.01); *A61B 5/6824* (2013.01);
(Continued)

(58) Field of Classification Search
None
See application file for complete search history.

(56) References Cited

U.S. PATENT DOCUMENTS 6,042,555 A * 3/2000 Kramer et al. ............... 600/595
7,812,826 B2 * 10/2010 Ording et al. ............... 345/173
(Continued)

FOREIGN PATENT DOCUMENTS

CN 1531676 9/2004
CN 1996208 7/2007
(Continued)

OTHER PUBLICATIONS

European Patent Office Application Serial No. 13176759.2, Search Report dated Sep. 5, 2014, 6 pages.
(Continued)

*Primary Examiner* — Dismery Mercedes
(74) *Attorney, Agent, or Firm* — Lee, Hong, Degerman, Kang & Waimey

(57) ABSTRACT

A terminal wearable by a user and a control method thereof are provided. The terminal includes: a body configured to wrap at least one region of a wrist and detachably formed; a sensing unit disposed in one surface of the body and configured to sense a movement of at least one of tendons passing through the wrist and the wrist; and a controller configured to generate a control signal for controlling an external device to execute a function previously matched to the sensed movement of the at least one of the tendons and the wrist.

12 Claims, 31 Drawing Sheets

(51) Int. Cl.

| | | |
|---|---|---|
| *A61B 5/11* | (2006.01) | |
| *G06F 3/03* | (2006.01) | |
| *G06F 3/0484* | (2013.01) | |
| *G06F 9/44* | (2006.01) | |
| *G06F 1/16* | (2006.01) | |

(52) U.S. Cl.
CPC ............ *G06F 1/163* (2013.01); *G06F 1/1652* (2013.01); *G06F 3/011* (2013.01); *G06F 3/013* (2013.01); *G06F 3/014* (2013.01); *G06F 3/015* (2013.01); *G06F 3/0304* (2013.01); *G06F 3/04842* (2013.01); *G06F 3/04845* (2013.01); *G06F 9/4446* (2013.01); *A61B 5/721* (2013.01); *G09G 2380/02* (2013.01)

(56) References Cited

U.S. PATENT DOCUMENTS

| | | | | | |
|---|---|---|---|---|---|
| 8,519,950 | B2* | 8/2013 | Radivojevic | ............ | G06F 3/014 345/156 |
| 8,743,052 | B1* | 6/2014 | Keller | ............ | G06F 3/014 345/156 |
| 2002/0009972 | A1* | 1/2002 | Amento | ............ | G06F 3/017 455/66.1 |
| 2004/0155870 | A1* | 8/2004 | Middleton | ............ | G04G 21/08 345/173 |
| 2004/0193413 | A1* | 9/2004 | Wilson | ............ | G06F 3/017 704/243 |
| 2005/0237296 | A1* | 10/2005 | Lee | ............ | 345/156 |
| 2008/0170776 | A1* | 7/2008 | Albertson et al. | ............ | 382/154 |
| 2008/0291225 | A1 | 11/2008 | Arneson | | |
| 2009/0051648 | A1* | 2/2009 | Shamaie | ............ | G06F 3/0346 345/156 |
| 2009/0103780 | A1* | 4/2009 | Nishihara | ............ | G06F 3/017 382/103 |
| 2009/0274339 | A9* | 11/2009 | Cohen | ............ | G06K 9/00348 382/103 |
| 2009/0315740 | A1* | 12/2009 | Hildreth et al. | ............ | 341/20 |
| 2010/0029327 | A1* | 2/2010 | Jee | ............ | G04G 17/045 455/556.1 |
| 2010/0066664 | A1* | 3/2010 | Son | ............ | G06F 1/163 345/156 |
| 2010/0117975 | A1* | 5/2010 | Cho | ............ | G06F 1/1626 345/173 |
| 2010/0275159 | A1* | 10/2010 | Matsubara | ............ | G06F 3/011 715/810 |
| 2010/0289740 | A1* | 11/2010 | Kim et al. | ............ | 345/157 |
| 2010/0302137 | A1* | 12/2010 | Benko | ............ | G06F 3/005 345/156 |
| 2011/0054360 | A1* | 3/2011 | Son | ............ | A61B 5/1126 600/595 |
| 2011/0054782 | A1* | 3/2011 | Kaahui | ............ | A61B 5/1107 701/532 |
| 2011/0148568 | A1* | 6/2011 | Lim | ............ | G05B 19/042 340/4.31 |
| 2011/0296353 | A1* | 12/2011 | Ahmed et al. | ............ | 715/848 |
| 2012/0044139 | A1* | 2/2012 | Kim | ............ | H04N 5/4403 345/157 |
| 2012/0127070 | A1* | 5/2012 | Ryoo | ............ | G06F 3/014 345/156 |
| 2012/0249409 | A1* | 10/2012 | Toney | ............ | G06F 3/017 345/156 |
| 2012/0262574 | A1* | 10/2012 | Park | ............ | G06F 3/017 348/143 |
| 2012/0316456 | A1 | 12/2012 | Rahman et al. | | |
| 2012/0319940 | A1* | 12/2012 | Bress | ............ | G06F 3/017 345/156 |
| 2013/0120106 | A1* | 5/2013 | Cauwels | ............ | G06F 1/163 340/3.1 |
| 2013/0120459 | A1* | 5/2013 | Dickinson et al. | ............ | 345/650 |
| 2013/0222271 | A1* | 8/2013 | Alberth | ............ | G06F 1/163 345/173 |
| 2013/0278504 | A1* | 10/2013 | Tong | ............ | G06F 3/017 345/158 |
| 2014/0139454 | A1* | 5/2014 | Mistry | ............ | G06F 3/041 345/173 |

FOREIGN PATENT DOCUMENTS

| | | |
|---|---|---|
| CN | 101640712 | 2/2010 |
| CN | 102339626 | 2/2012 |
| EP | 1408443 | 4/2004 |
| EP | 2150031 | 2/2010 |
| WO | 2011/055326 | 5/2011 |

OTHER PUBLICATIONS

European Patent Office Application Serial No. 13176759.2 Search Report dated Feb. 6, 2015, 13 pages.

The State Intellectual Property Office of the People's Republic of China Application Serial No. 201310319717.8, Office Action dated Feb. 2, 2015, 11 pages.

The State Intellectual Property Office of the People's Republic of China Application Serial No. 201310319717.8, Office Action dated Jul. 29, 2015, 8 pages.

* cited by examiner

FIG. 4A
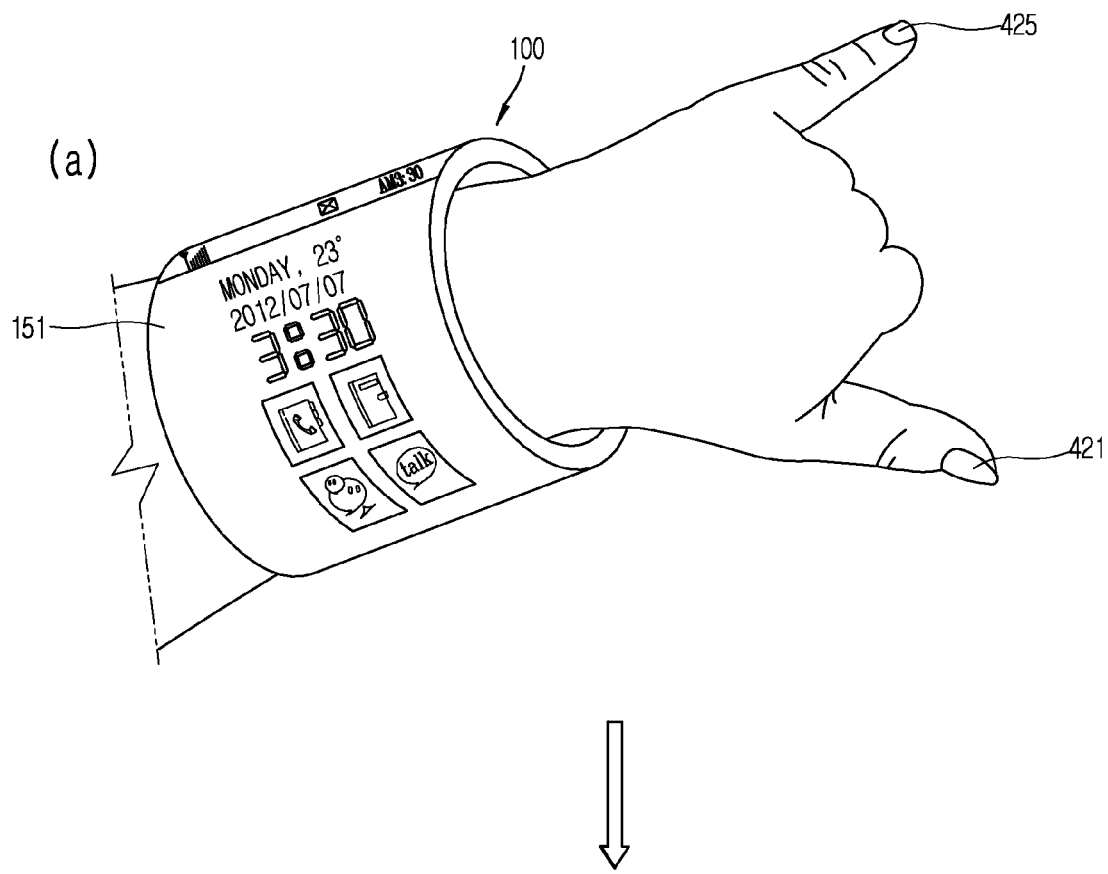
(a)
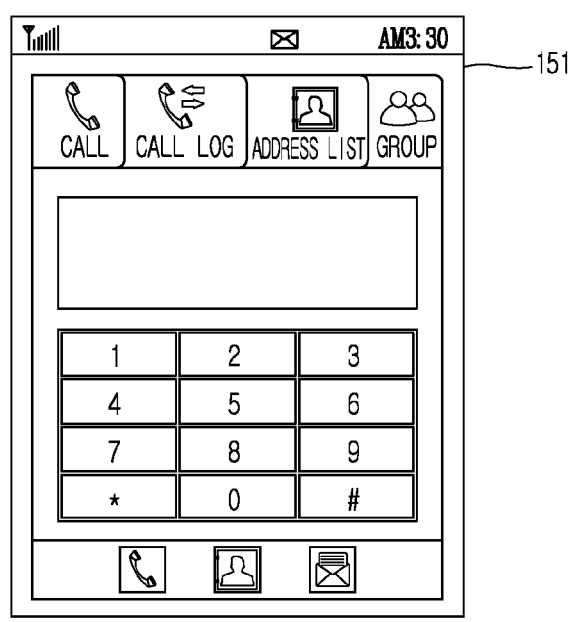
(b)

FIG. 4B
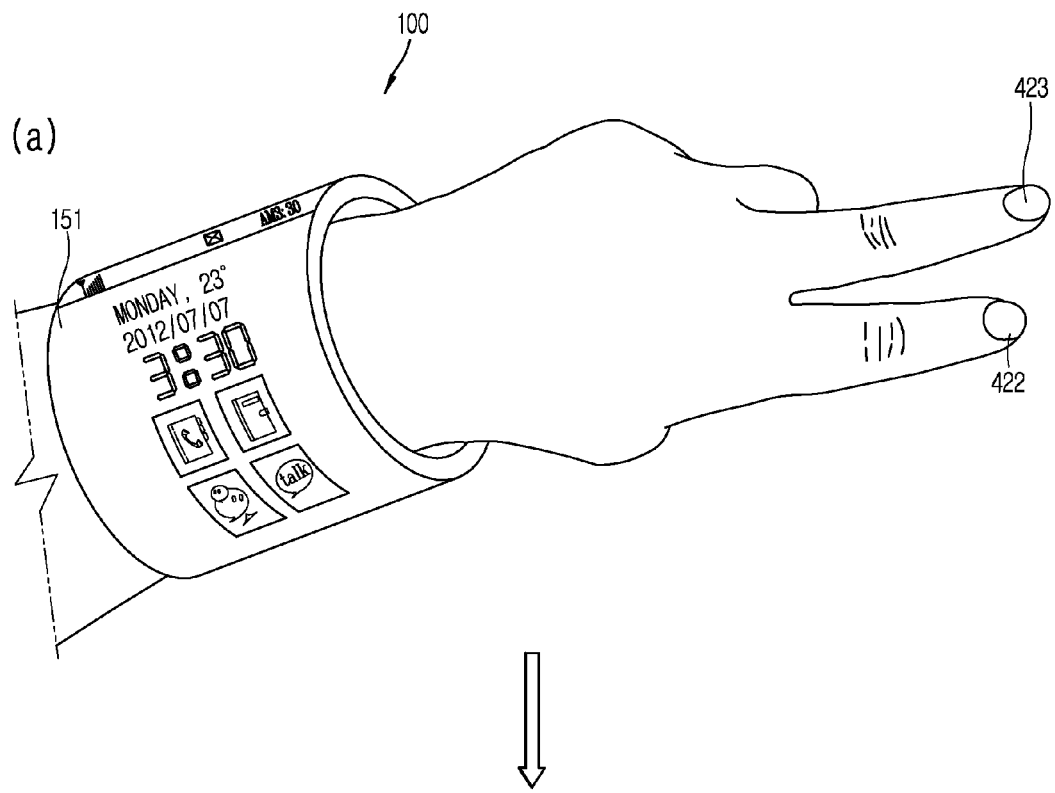
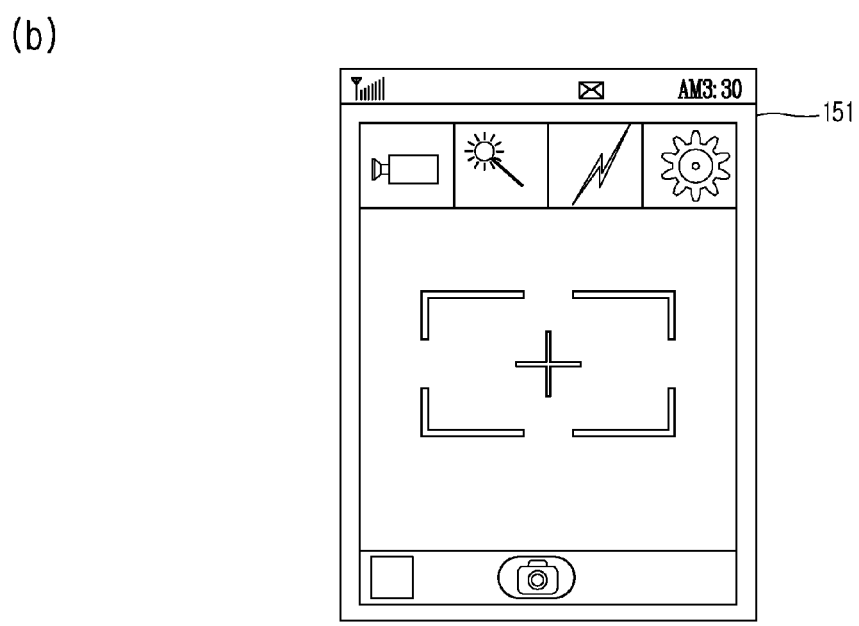

FIG. 5A
(a)
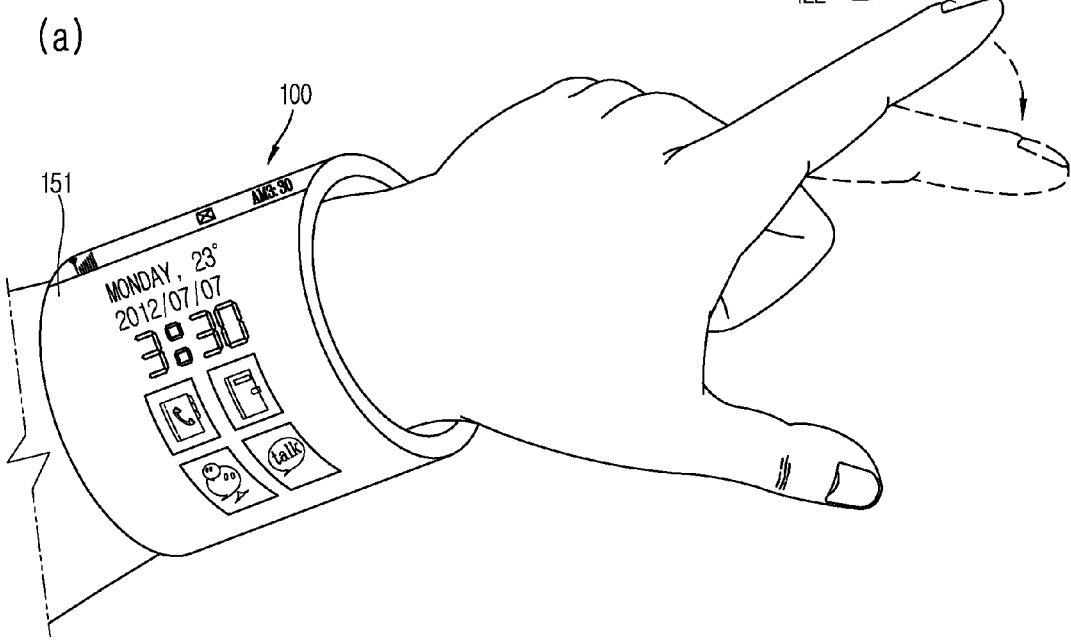
(b)
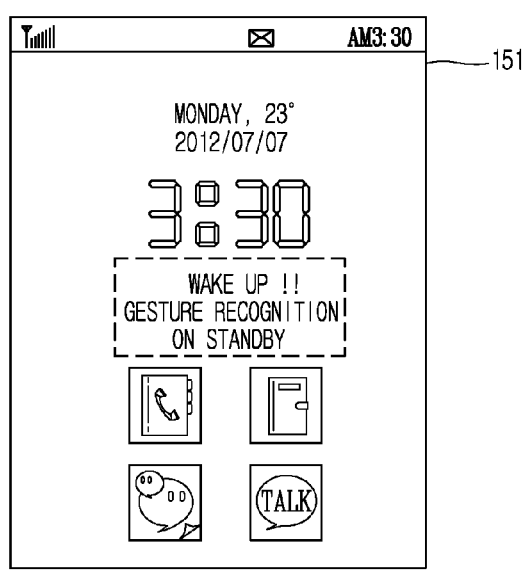

FIG. 6A
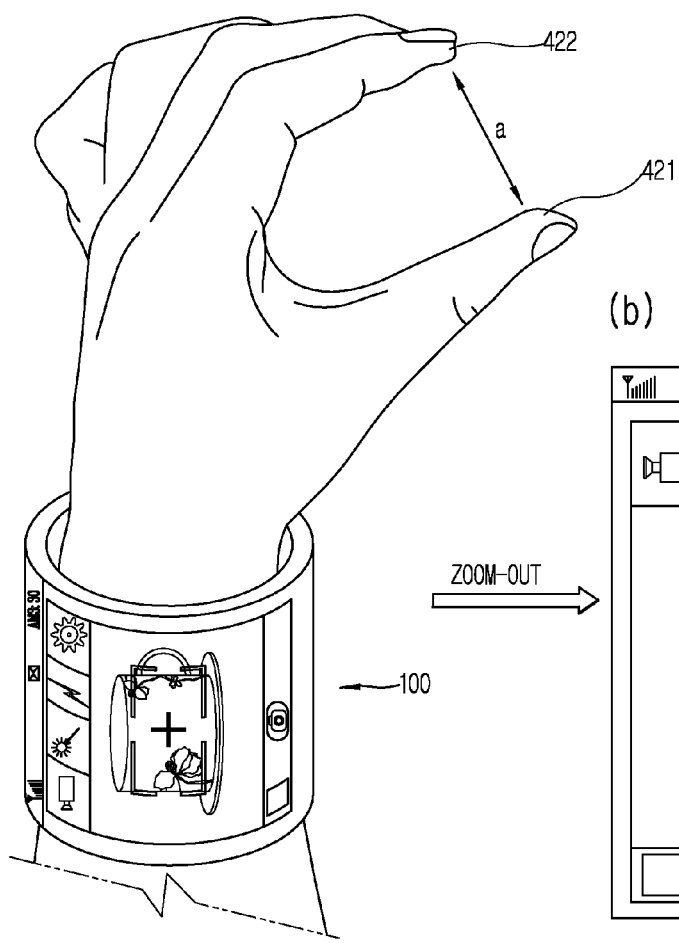
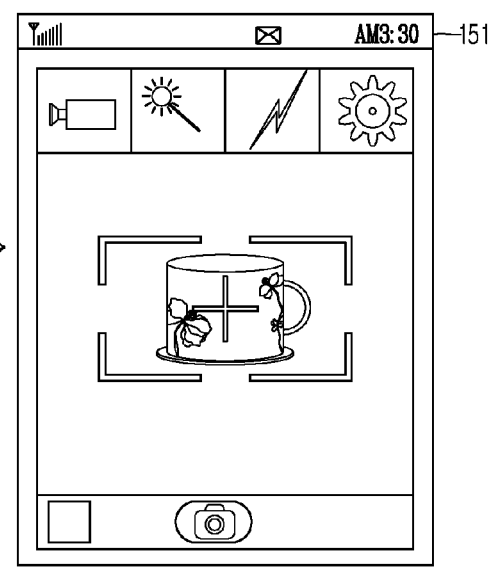

FIG. 7B
(a)
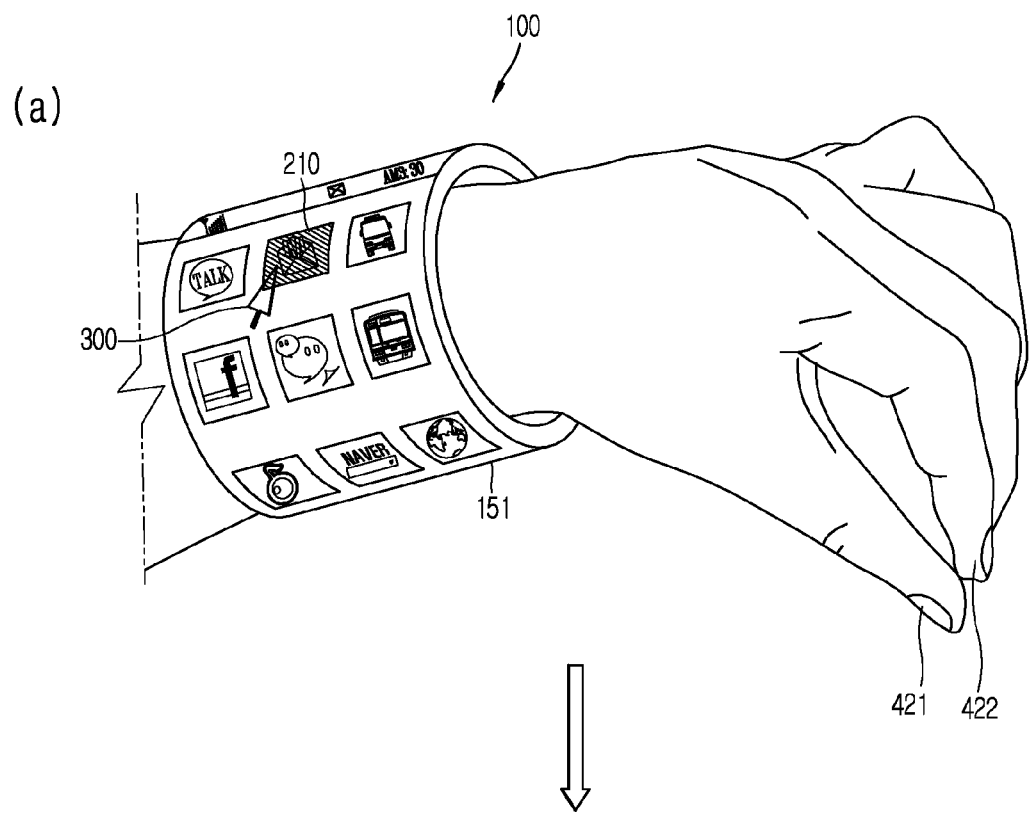
(b)
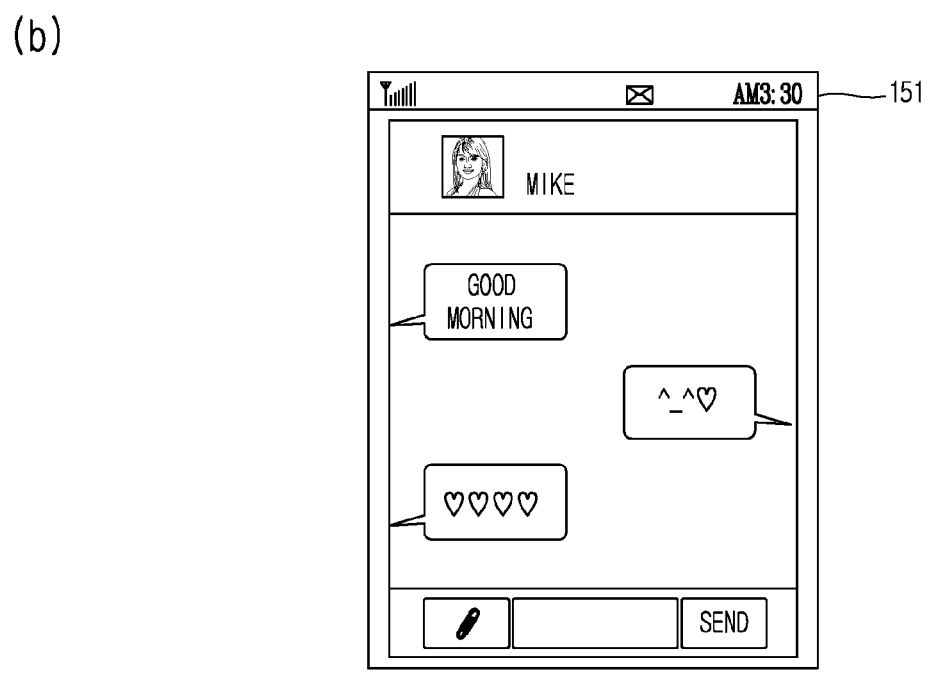

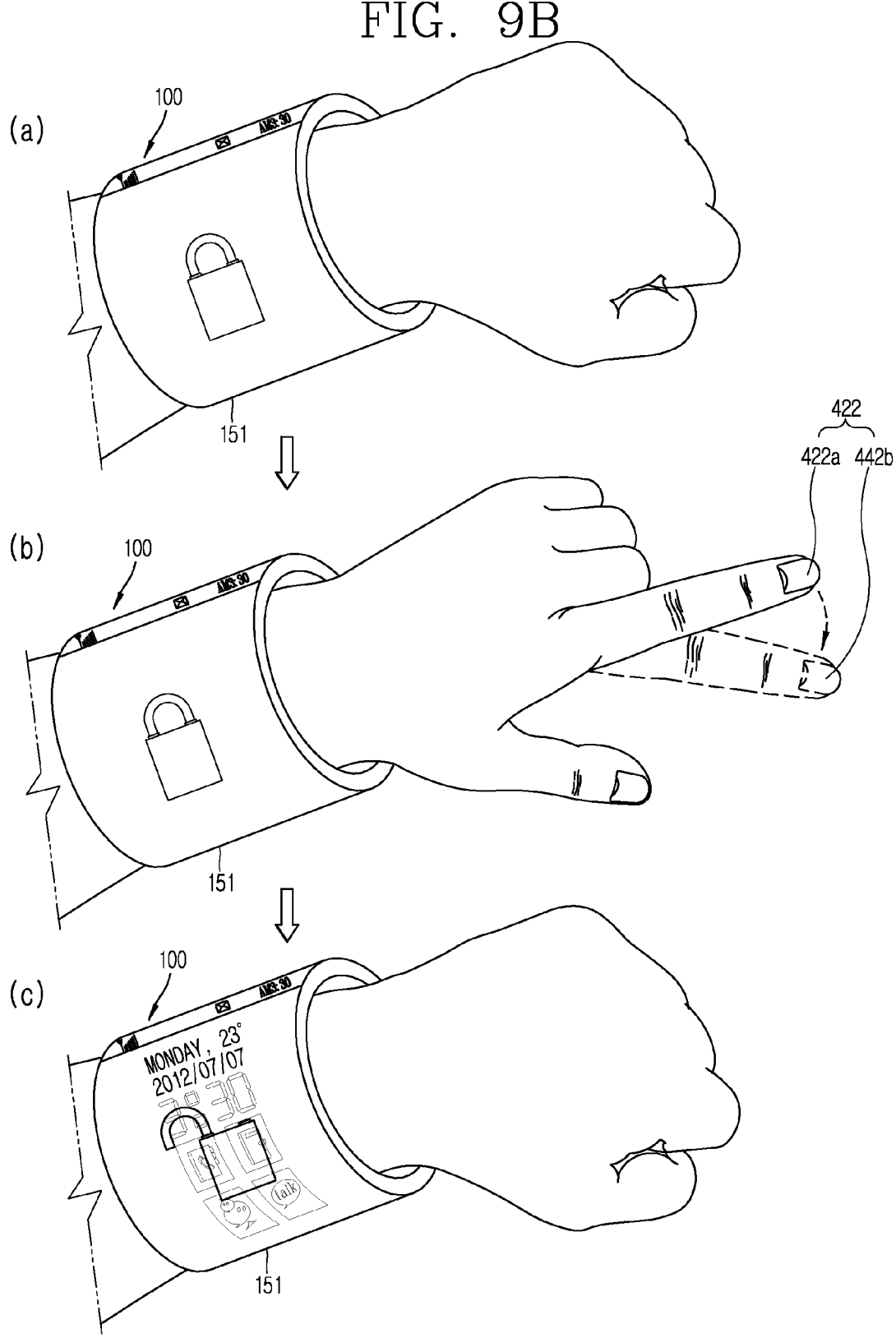

FIG. 10B
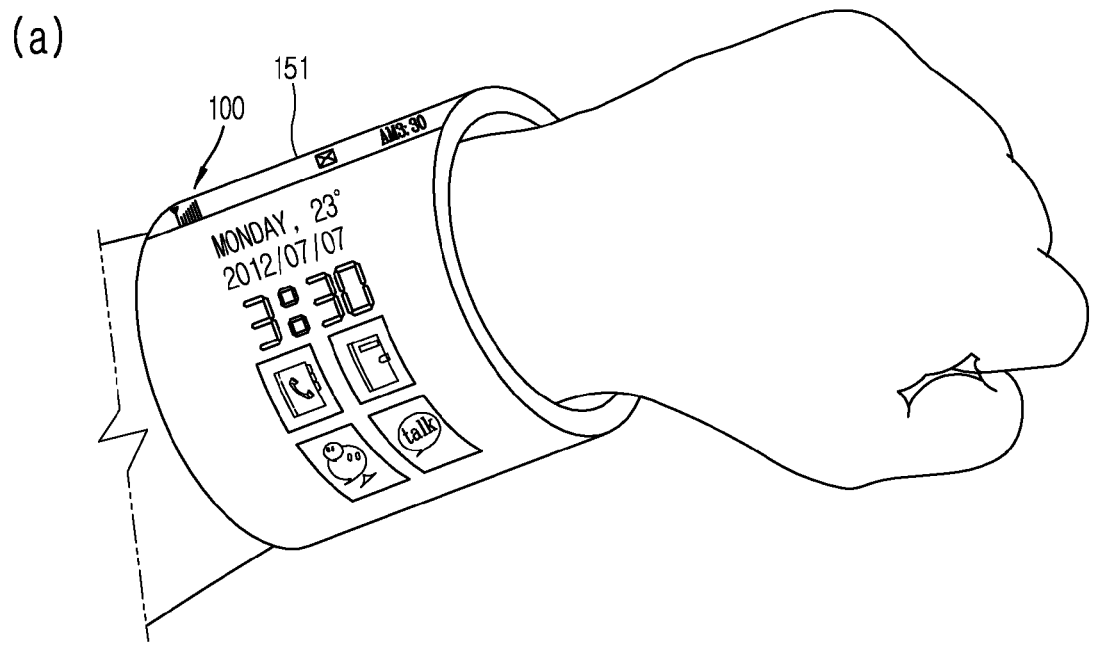
(a)
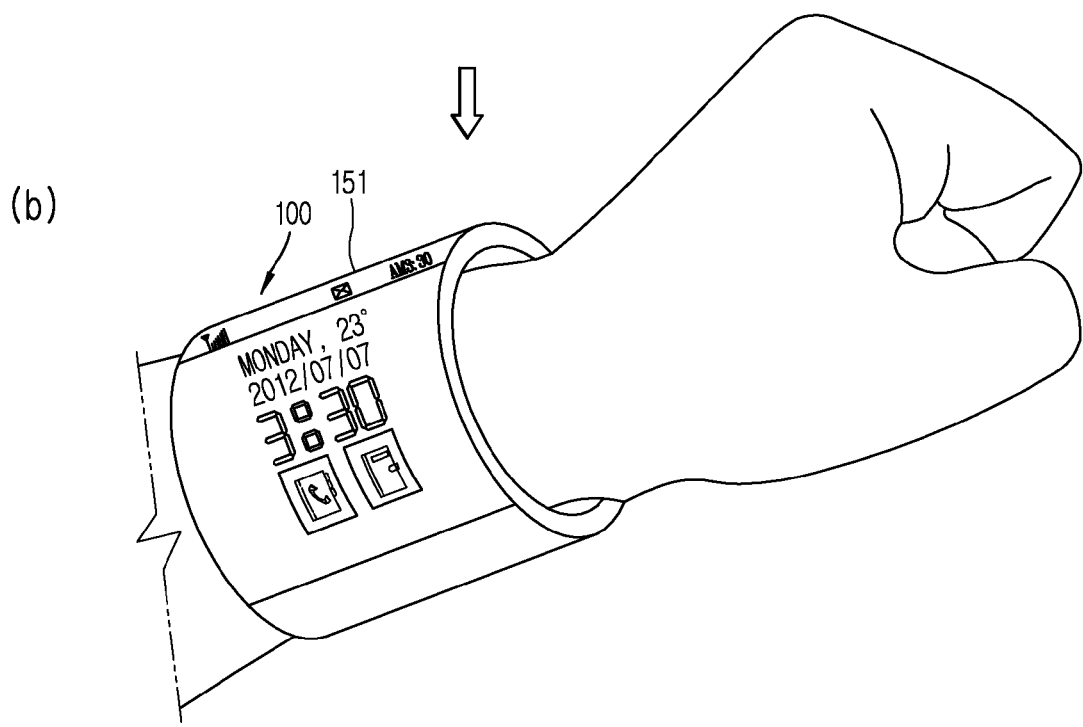
(b)

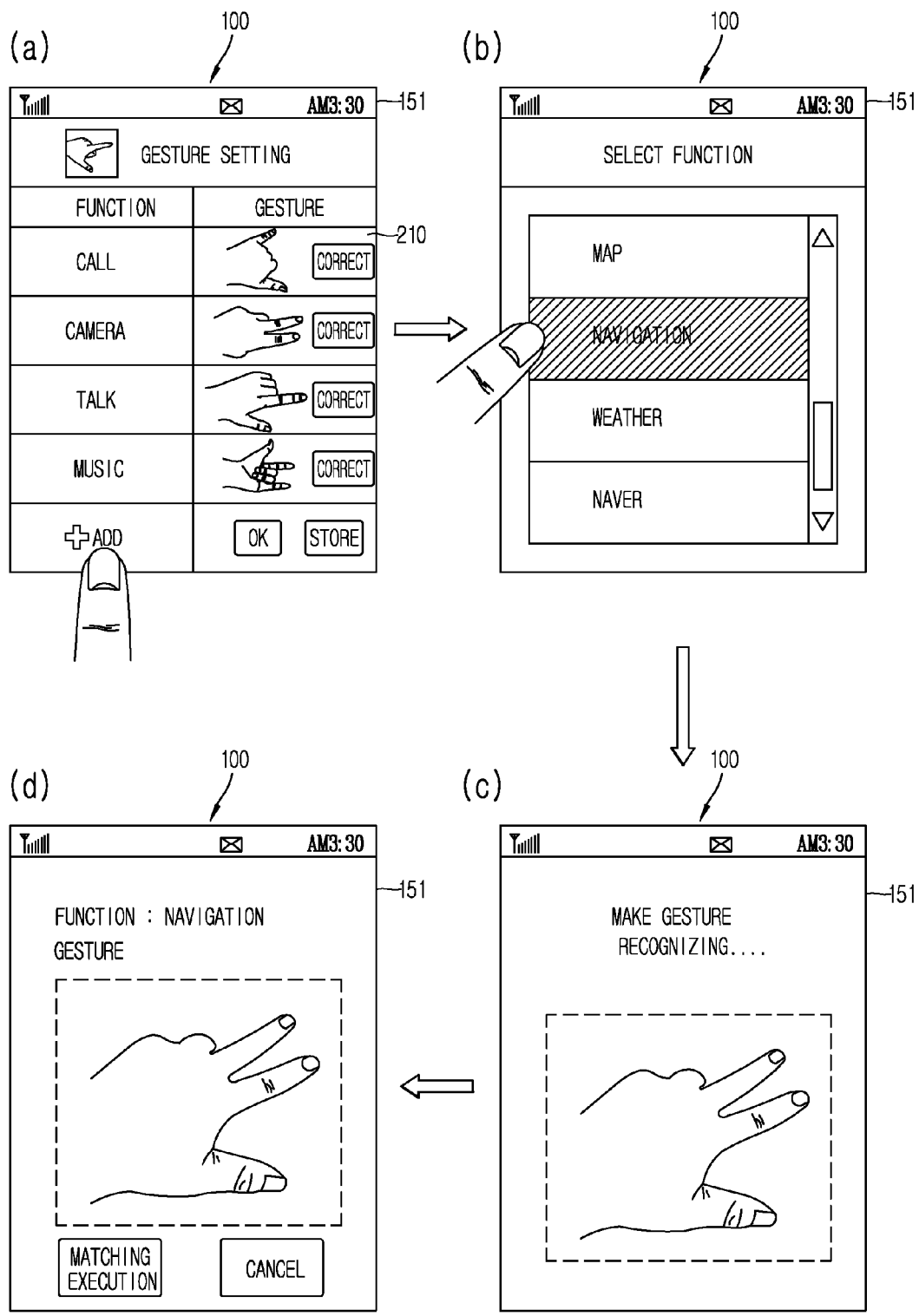

FIG. 18
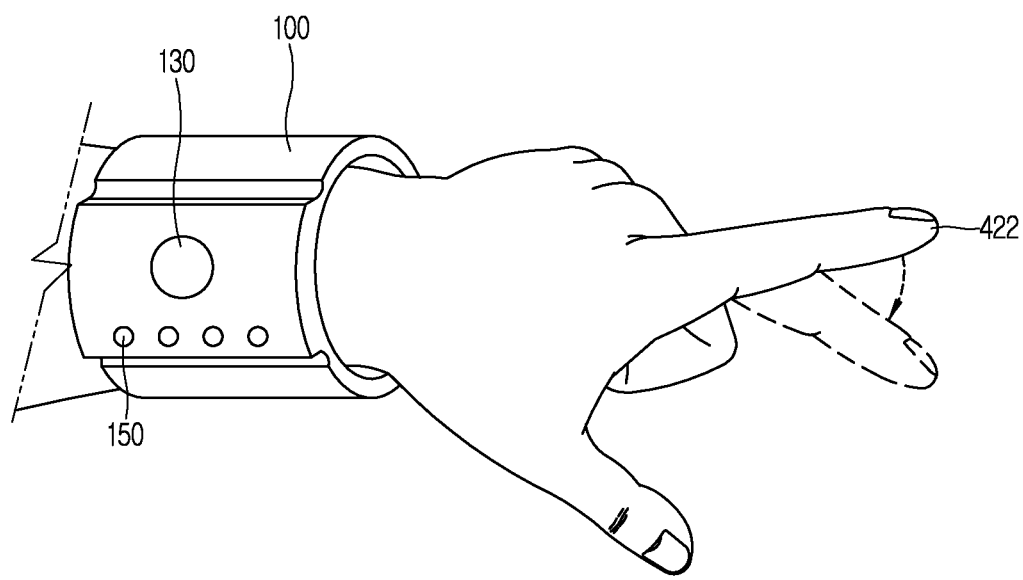
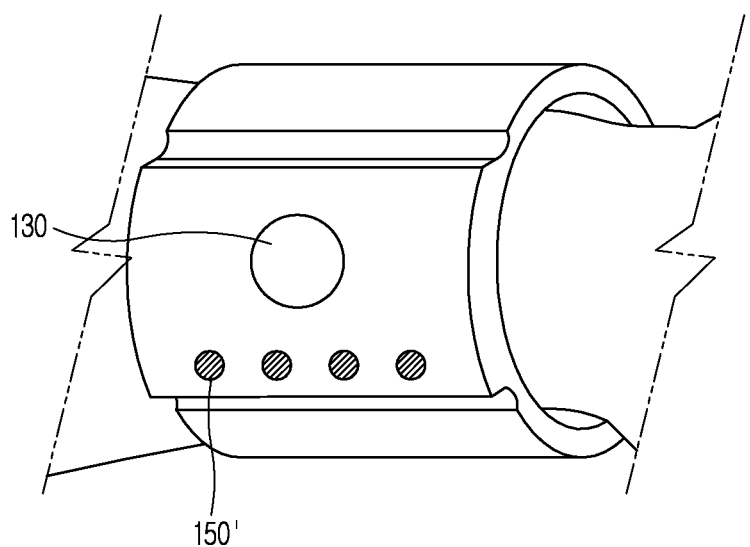

TERMINAL AND CONTROL METHOD THEREOF

CROSS REFERENCE TO RELATED APPLICATIONS

Pursuant to 35 U.S.C. §119(a), this application claims the benefit of earlier filing date and right of priority to Korean Application No. 10-2012-0082721, filed on Jul. 27, 2012 and No. 10-2013-0028204, filed on Mar. 15, 2013, the contents of which is incorporated by reference herein in its entirety.

BACKGROUND OF THE INVENTION

Field of the Invention

The present invention relates to a terminal that a user may wear (or a user-wearable terminal) and a control method thereof.

Description of the Related Art

In general, terminals may be divided into a terminal (a mobile terminal or a portable terminal) and stationary terminal according to whether or not terminals are movable. In addition, terminals may be divided into a handheld terminal and a vehicle mount terminal according to whether or not users can directly carry it around.

As such functions become more diversified, the terminal can support more complicated functions such as capturing images or video, reproducing music or video files, playing games, receiving broadcast signals, and the like. By comprehensively and collectively implementing such functions, the terminal may be embodied in the form of a multimedia player or device. Efforts are ongoing to support and increase the functionality of terminals. Such efforts include software and hardware improvements, as well as changes and improvements in the structural components which form the terminal.

A terminal may generate a control signal for controlling an external device such as a remote controller. The terminal that controls an external device from a remote area has evolved toward having a user wearable design, so a wearable terminal has come into prominence. With wearable terminals, the necessity of a user-friendly user interface using body characteristics has emerged.

SUMMARY OF THE INVENTION

An aspect of the present invention is to provide a terminal generating a control signal by using features sensed from a user's wrist, and a control method thereof.

Another aspect of the present invention is to provide a terminal capable of generating a control command on the basis of movements of tendons passing through a user's wrist by using the characteristics of a flexible display unit that can be bowed or bowed, and a control method thereof.

According to an embodiment of the present invention, there is provided a terminal including: a body configured to wrap at least one region of a wrist and detachably formed; a sensing unit disposed in one surface of the body and configured to sense a movement of at least one of tendons passing through the wrist and the wrist; and a controller configured to generate a control signal for controlling an external device to execute a function previously matched to the sensed movement of the at least one of the tendons and the wrist.

In an embodiment of the present invention, the terminal may further include a flexible display unit formed in at least one region of the body and configured to be bowable.

In an embodiment of the present invention, the controller may generate control signals for executing different functions corresponding to different movement characteristics of the tendons, respectively, and the movement characteristics of the tendons may be related to at least one of a shape of a user's finger(s), a movement speed of the user's finger, a movement speed of a hand, and a change in grasping power.

In an embodiment of the present invention, only when a pre-set starting gesture is sensed, the controller may execute a function corresponding to the movement characteristics of the tendons sensed by the sensing unit.

In an embodiment of the present invention, on the basis of sensing of the pre-set starting gesture, guidance information related to functions matched to different movement characteristics according to different movements of the tendons, respectively, may be displayed on the flexible display unit.

In an embodiment of the present invention, when a shape of the user's finger corresponds to a first gesture, the controller may execute a first function, and when the shape of the user's finger corresponds to a second gesture, the controller may execute a second function, wherein the first function may be a camera function and the second function may be a music execution function.

In an embodiment of the present invention, when the camera function is executed on the basis of sensing of the first gesture, the controller may generate a control signal for controlling a function related to the camera on the basis of a change in the shape of the user's finger.

In an embodiment of the present invention, as movements of the tendons are sensed, the controller may estimate a distance between the first finger and the second finger, and control a zoom-in or zoom-out function according to the estimated distance.

In an embodiment of the present invention, the terminal may include a plurality of cameras disposed in different positions, and the controller may control at least one of the plurality of cameras such that activated cameras, among the plurality of cameras, are changed according to a direction in which the wrist faces.

In an embodiment of the present invention, the terminal may include a camera sensor, and the controller may control a position of a display region in which information is displayed on the flexible display unit, on the basis of a direction of user's eyes sensed by the camera sensor.

In an embodiment of the present invention, the controller may move the information displayed in the display region, on the basis of a movement of the wrist sensed by the sensing unit.

In an embodiment of the present invention, the controller may select at least one of one or more selection target items included in the information displayed in the display region, on the basis of the movements of tendons changing according to a movement of the user's finger.

In an embodiment of the present invention, a graphic object whose position is changed according to the movement of the user's finger may be displayed in the display region.

In an embodiment of the present invention, at least one of the selection target items may be selected on the basis of sensing of movements of the tendons corresponding to hitting of at least two of the plurality of fingers.

In an embodiment of the present invention, the controller may determine a position in which the flexible display unit wraps the wrist on the basis of an area in which the sensing unit and the wrist are in contact, and control a size of a display region in which information is displayed according to the determined position.

In an embodiment of the present invention, sensitivity of the sensing unit that senses movements of the tendons may be controlled to be different according to a position wrapped by the flexible display unit.

In an embodiment of the present invention, the terminal may further include: a wireless communication unit configured to transmit the generated control signal to the external device.

In an embodiment of the present invention, the controller may transmit a control signal corresponding to the movement characteristics to the external device only when a pre-set starting gesture is sensed.

In an embodiment of the present invention, the sensing unit may include: a physical signal sensing unit configured to sense a movement of at least one of the tendons and the wrist; and a bio-signal sensing unit configured to sense a bio-signal measurable from the wrist, wherein the controller may generate a control signal by using the at least one sensed movement and the bio-signal.

In an embodiment of the present invention, the wireless communication unit may transmit the sensed bio-signal to the external device together with the generated control signal.

Further scope of applicability of the present invention will become apparent from the detailed description given hereinafter. However, it should be understood that the detailed description and specific examples, while indicating preferred embodiments of the invention, are given by illustration only, since various changes and modifications within the spirit and scope of the invention will become apparent to those skilled in the art from this detailed description.

BRIEF DESCRIPTION OF THE DRAWINGS

The present invention will become more fully understood from the detailed description given hereinbelow and the accompanying drawings, which are given by illustration only, and thus are not limitative of the present invention, and wherein:

FIGS. 4A and 4B are conceptual views illustrating the control method of FIG. 3 in the terminal according to an embodiment of the present invention.

FIGS. 5A and 5B are conceptual views illustrating a method for receiving a preparatory movement in the terminal according to an embodiment of the present invention.

FIGS. 6A, 6B, 6C, 7A, 7B, 8A, and 8B are conceptual views illustrating methods for generating various control signals according to different motion characteristics in the terminal according to an embodiment of the present invention.

FIGS. 9A and 9B are conceptual views illustrating a method for performing a security-related function on the basis of movement characteristics of tendons in the terminal according to an embodiment of the present invention.

FIGS. 10A and 10B are conceptual views illustrating a method for displaying information on a flexible display unit in the terminal according to an embodiment of the present invention.

FIG. 11 is a conceptual view illustrating a method for setting a function corresponding to motion characteristics in the terminal according to an embodiment of the present invention.

FIG. 18 is a conceptual view illustrating a method for receiving a preparatory movement in the terminal according to an embodiment of the present invention.

DETAILED DESCRIPTION OF THE INVENTION

The embodiments of the present invention will now be described with reference to the accompanying drawings, in which like numbers refer to like elements throughout although the embodiments are different, and a description of the like elements a first embodiment will be used for those of the different embodiment. In the following description, usage of suffixes such as 'module', 'part' or 'unit' used for referring to elements is given merely to facilitate explanation of the present invention, without having any significant meaning by itself. In describing the present invention, if a detailed explanation for a related known function or construction is considered to unnecessarily divert the gist of the present invention, such explanation has been omitted but would be understood by those skilled in the art. The accompanying drawings of the present invention aim to facilitate understanding of the present invention and should not be construed as limited to the accompanying drawings.

Terminals described in the present disclosure may include mobile phones, smart phones, notebook computers, tablet computers, digital broadcast receivers, PDAs (Personal Digital Assistants), PMPs (Portable Multimedia Player), navigation devices, slate PCs, tablet PCs, ultra-books, and the like. However, it would be understood by a person skilled in the art that the configuration according to embodiments of the present invention can be also applicable to the fixed types of terminals such as digital TVs, desk top computers, and the like, except for any elements especially configured for a mobile purpose.

Figure 1:
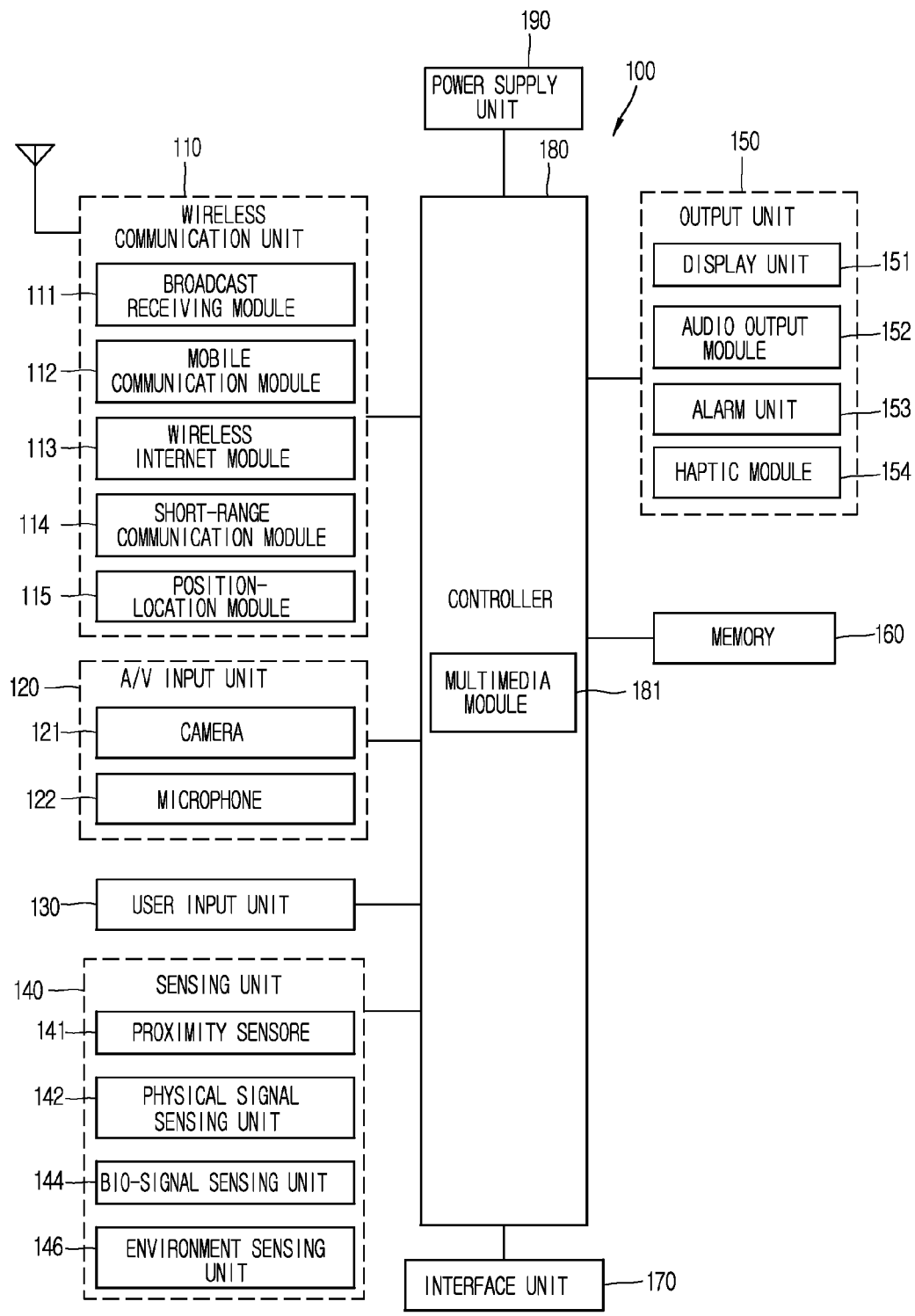
FIG. 1 is a block diagram of a terminal according to an embodiment of the present invention.

FIG. 1 is a block diagram of a terminal according to an embodiment of the present invention.

The terminal 100 may include a wireless communication unit 110, an A/V (Audio/Video) input unit 120, a user input unit 130, a sensing unit 140, an output unit 150, a memory 160, an interface unit 170, a controller 180, and a power supply unit 190, etc. FIG. 1 shows the terminal as having various components, but it should be understood that implementing all of the illustrated components is not a requirement. Greater or fewer components may alternatively be implemented.

The elements of the terminal will be described in detail as follows.

The wireless communication unit 110 typically includes one or more modules allowing radio communication between the terminal 100 and a wireless communication system or a network in which the terminal is located. For example, the wireless communication unit may include at least one of a broadcast receiving module 111, a mobile communication module 112, a wireless Internet module 113, a short-range communication module 114, and a location information module 115.

The broadcast receiving module 111 receives broadcast signals and/or broadcast associated information from an external broadcast management server (or other network entity) via a broadcast channel.

The broadcast channel may include a satellite channel and/or a terrestrial channel. The broadcast management server may be a server that generates and transmits a broadcast signal and/or broadcast associated information or a server that receives a previously generated broadcast signal and/or broadcast associated information and transmits the same to a terminal. The broadcast signal may include a TV broadcast signal, a radio broadcast signal, a data broadcast signal, and the like. Also, the broadcast signal may further include a broadcast signal combined with a TV or radio broadcast signal.

The broadcast associated information may refer to information associated with a broadcast channel, a broadcast program or a broadcast service provider. The broadcast associated information may also be provided via a mobile communication network and, in this case, the broadcast associated information may be received by the mobile communication module 112.

The broadcast associated information may exist in various forms. For example, it may exist in the form of an electronic program guide (EPG) of digital multimedia broadcasting (DMB), electronic service guide (ESG) of digital video broadcast-handheld (DVB-H), and the like.

The broadcast receiving module 111 may be configured to receive signals broadcast by using various types of broadcast systems. In particular, the broadcast receiving module 111 may receive a digital broadcast by using a digital broadcast system such as multimedia broadcasting-terrestrial (DMB-T), digital multimedia broadcasting-satellite (DMB-S), digital video broadcast-handheld (DVB-H), the data broadcasting system known as media forward link only (MediaFLO®), integrated services digital broadcast-terrestrial (ISDB-T), etc. The broadcast receiving module 111 may be configured to be suitable for every broadcast system that provides a broadcast signal as well as the above-mentioned digital broadcast systems.

Broadcast signals and/or broadcast-associated information received via the broadcast receiving module 111 may be stored in the memory 160.

The mobile communication module 112 transmits and/or receives radio signals to and/or from at least one of a base station, an external terminal and a server. Such radio signals may include a voice call signal, a video call signal or various types of data according to text and/or multimedia message transmission and/or reception.

The wireless Internet module 113 supports wireless Internet access for the terminal. This module may be internally or externally coupled to the terminal. The wireless Internet access technique implemented may include a WLAN (Wireless LAN) (Wi-Fi), Wibro (Wireless broadband), Wimax (World Interoperability for Microwave Access), HSDPA (High Speed Downlink Packet Access), or the like.

The short-range communication module 114 is a module for supporting short range communications. Some examples of short-range communication technology include Bluetooth™, Radio Frequency IDentification (RFID), Infrared Data Association (IrDA), Ultra-WideBand (UWB), ZigBee™, and the like.

The location information module 115 is a module for checking or acquiring a location (or position) of the terminal. A typical example of the location information module is a GPS (Global Positioning System).

Referring to FIG. 1, the A/V input unit 120 is configured to receive an audio or video signal. The A/V input unit 120 may include a camera 121 and a microphone 122. The camera 121 processes image data of still pictures or video obtained by an image capture device in a video capturing mode or an image capturing mode. The processed image frames may be displayed on a display unit 151.

The image frames processed by the camera 121 may be stored in the memory 160 (or other storage medium) or transmitted via the wireless communication unit 110. Two or more cameras 121 may be provided according to the configuration of the terminal.

The microphone 122 may receive sounds (audible data) via a microphone in a phone call mode, a recording mode, a voice recognition mode, and the like, and can process such sounds into audio data. The processed audio (voice) data may be converted for output into a format transmittable to a mobile communication base station via the mobile communication module 112 in case of the phone call mode. The microphone 122 may implement various types of noise canceling (or suppression) algorithms to cancel (or suppress) noise or interference generated in the course of receiving and transmitting audio signals.

The user input unit 130 may generate input data from commands entered by a user to control various operations of the terminal. The user input unit 130 may include a keypad, a dome switch, a touch pad, a jog wheel, a jog switch, and the like.

The sensing unit 140 detects a current status (or state) of the terminal 100 such as an opened or closed state of the terminal 100, a location of the terminal 100, the presence or absence of user contact with the terminal 100 (i.e., touch inputs), the orientation of the terminal 100, an acceleration or deceleration movement and direction of the terminal 100, etc., and generates commands or signals for controlling the operation of the terminal 100. For example, when the terminal 100 is implemented as a slide type mobile phone, the sensing unit 140 may sense whether the slide phone is opened or closed. In addition, the sensing unit 140 can detect whether or not the power supply unit 190 supplies power or whether or not the interface unit 170 is coupled with an external device.

The sensing unit 140 may include a physical signal sensing unit 142, an environment sensing unit 146, and a bio-signal sensing unit 144.

The physical signal sensing unit 142 measures a physical change in a body of the terminal 100. For example, the physical signal sensing unit 142 may measure acceleration or angular velocity of a movement or a change in pressure generated by a tendon of a user's wrist.

The environment sensing unit 146 may measure information regarding an environment around the terminal 100 such as altitude, atmospheric pressure, a temperature, humidity, intensity of illumination, and the like.

The bio-signal sensing unit 144 refers to a sensor sensing a bio-signal generated in the body of a user. The bio-signal refers to an electrical signal generated by a bodily tissue such as a micro-cell, or the like, of a human. Major electrical measures include electro-encephalogram (EEG), electrocardiogram (ECG), electromyogram (EMG), ocular electrical conductivity, and a galvanic skin reflex (GSR), and major physical measures include blood pressure, a heart rate, arrhythmia, stroke quotient, pulsation defect, a body temperature, a breathing rate, and the like.

An electrocardiogram (ECG) sensor refers to a sensor measuring an electrical activity of a heart from a surface of the skin. The ECG sensor measures an action current generated by myocardium (heart muscle) according to heartbeat with an ammeter by inducing it to two appropriate portions of a body surface. The ECG may measure a disease related to heart such as arrhythmia, cardiovascular disease, and the like. For example, the ECG sensor may include, for example, a necklace-type ECG sensor and a patch-type ECG sensor.

The electromyogram (EMG) sensor refers to a sensor measuring contractile force, muscle activity, and fatigability of muscle from the surface of a skin. An EMG measurement scheme of the EMG sensor includes a surface deriving scheme of attaching an electrode to the surface of a human skin and inducing a potential, and a needle electrode scheme of sticking a needle electrode to a muscle, deriving an activity potential formed in a spot in the muscle to detect activity in units of motion.

The electroencephalogram (EEG) sensor refers to a sensor measuring concentration or brain activity with respect to an extrastimulation from the surface of a skin. The EEG sensor induces potential fluctuation made in a brain of a human or a brain current caused by the potential fluctuation from scalp and measures an electrogram. Namely, the EGG sensor may measure brain waves with respect to respective regions (e.g., the frontal lobe, a temporal lobe, and the occipital lobe) of a brain.

The galvanic skin reflex (GSR) sensor measures a change in skin resistance with respect to sympathetic nerve activity from a surface of a skin. The GSR sensor measures a phenomenon that electrical resistance is temporarily reduced, action potential is generate, and the like, due to an external stimulus or emotional excitement in the skin of a living body. The GSR sensor may also be used as a lie detector.

A photoplethysmography (PPG) sensor may measure a blood flow rate of a peripheral blood vessel by an optical sensor and may measure oxygen saturation and hardening of arteries. The PPG sensor may measure a blood flow rate by converting infrared light which has passed through capillary of a user's finger, excluding an amount of light absorbed to a receiving unit, into a current value. The PPG sensor may also measure oxygen saturation, pulsation, blood pressure, or a body temperature, as well as a blood flow rate.

An oxygen saturation ($SpO_2$) sensor measures a blood flow rate of a peripheral blood vessel by an optical sensor, and also measures blood oxygen saturation and pulsation. The $SpO_2$ sensor may sense whether oxygen saturation is abnormal by using a reference value with respect to arterial blood and venous blood, respectively.

An ultrasound sensor outputs a real time image of a fetus of a mother or an organ in a body. The ultrasound sensor detects a distance, a thickness, a movement, and the like, by generating ultrasonic waves having a frequency exceeding 20 kHz.

A blood pressure sensor measures blood pressure of artery by using pressure. The blood pressure sensor is used to measure blood information from a living body, which is classified into a pressure-electric conversion sensor such as electromanometer, a catheter tip blood pressure gauge (or a catheter tip sphygmomanometer), or the like, used in an invasive blood pressure measurement method.

A blood sugar sensor measures a numerical value of blood sugar by using an electrochemical action by collecting a small amount of blood from a user.

A polysomno sensor is a sensor for inspecting quality of sleep. The polysomno sensor inspects quality of sleep by synthetically measuring ECG, pulsation, respiration, oxygen saturation, brain waves, a body temperature, and the like.

A body composition sensor is a sensor for measuring a weight and body impedance and analyzing a weight, a body mass, body fat, a muscle mass, a metabolic rate. A body composition refers to body water, protein, minerals, and body fat, and the body composition sensor may measure a body composition by using bioelectrical impedance analysis.

The output unit 150 is configured to provide outputs in a visual, audible, and/or tactile manner (e.g., audio signal, video signal, alarm signal, vibration signal, etc.). The output unit 150 may include the display unit 151, an audio output module 152, an alarm unit 153, a haptic module 154, and the like.

The display unit 151 may display (output) information processed in the terminal 100. For example, when the terminal 100 is in a phone call mode, the display unit 151 may display a User Interface (UI) or a Graphic User Interface (GUI) associated with a call or other communication (such as text messaging, multimedia file downloading, etc.). When the terminal 100 is in a video call mode or image capturing mode, the display unit 151 may display a captured image and/or received image, a UI or GUI that shows videos or images and functions related thereto, and the like.

The display unit 151 may include at least one of a Liquid Crystal Display (LCD), a Thin Film Transistor-LCD (TFT-LCD), an Organic Light Emitting Diode (OLED) display, a flexible display, a three-dimensional (3D) display, and an e-ink display.

Some of them may be configured to be transparent or light-transmissive to allow viewing of the exterior, which may be called transparent displays. A typical transparent display may be, for example, a TOLED (Transparent Organic Light Emitting Diode) display, or the like. Through such configuration, the user can view an object positioned at the rear side of the terminal body through the region occupied by the display unit 151 of the terminal body.

The terminal 100 may include two or more display units according to its particular desired embodiment. For example, a plurality of display units may be separately or integrally disposed on one surface of the terminal, or may be separately disposed on mutually different surfaces.

Meanwhile, when the display unit 151 and a sensor (referred to as a 'touch sensor', hereinafter) for detecting a touch operation are overlaid in a layered manner to form a touch screen, the display unit 151 may function as both an input device and an output device. The touch sensor may have a form of a touch film, a touch sheet, a touch pad, and the like.

The touch sensor may be configured to convert pressure applied to a particular portion of the display unit 151 or a change in the capacitance or the like generated at a particular portion of the display unit 151 into an electrical input signal. The touch sensor may be configured to detect the pressure when a touch is applied, as well as the touched position and area.

When there is a touch input with respect to the touch sensor, a corresponding signal (signals) are transmitted to a touch controller. The touch controller processes the signals and transmits corresponding data to the controller 180. Accordingly, the controller 180 may recognize which portion of the display unit 151 has been touched.

Referring to FIG. 1, a proximity sensor 141 may be disposed within or near the touch screen. The proximity sensor 141 is a sensor for detecting the presence or absence of an object relative to a certain detection surface or an object that exists nearby by using the force of electromagnetism or infrared rays without a physical contact. Thus, the proximity sensor 141 has a considerably longer life span compared with a contact type sensor, and it can be utilized for various purposes.

Examples of the proximity sensor 141 may include a transmission type photoelectric sensor, a direct reflection type photoelectric sensor, a mirror-reflection type photoelectric sensor, an RF oscillation type proximity sensor, a capacitance type proximity sensor, a magnetic proximity sensor, an infrared proximity sensor, and the like. In case where the touch screen is the capacitance type, proximity of the pointer is detected by a change in electric field according to the proximity of the pointer. In this case, the touch screen (touch sensor) may be classified as a proximity sensor.

In the following description, for the sake of brevity, recognition of the pointer positioned to be close to the touch screen will be called a 'proximity touch', while recognition of actual contacting of the pointer on the touch screen will be called a 'contact touch'. In this case, when the pointer is in the state of the proximity touch, it means that the pointer is positioned to correspond vertically to the touch screen.

By employing the proximity sensor 141, a proximity touch and a proximity touch pattern (e.g., a proximity touch distance, a proximity touch speed, a proximity touch time, a proximity touch position, a proximity touch movement state, or the like) can be detected, and information corresponding to the detected proximity touch operation and the proximity touch pattern can be outputted to the touch screen.

The audio output module 152 may convert and output as sound audio data received from the wireless communication unit 110 or stored in the memory 160 in a call signal reception mode, a call mode, a record mode, a voice recognition mode, a broadcast reception mode, and the like. Also, the audio output module 152 may provide audible outputs related to a particular function performed by the terminal 100 (e.g., a call signal reception sound, a message reception sound, etc.). The audio output module 152 may include a speaker, a buzzer, or other sound generating device.

The alarm unit 153 may provide outputs to inform about the occurrence of an event of the terminal 100. Typical events may include call reception, message reception, key signal inputs, a touch input etc. In addition to audio or video outputs, the alarm unit 153 may provide outputs in a different manner to inform about the occurrence of an event. For example, the alarm unit 153 may provide an output in the form of vibrations. When a call, a message, or some other incoming communication is received, the alarm unit 153 may provide tactile outputs (i.e., vibrations) to inform the user thereof. By providing such tactile outputs, the user can recognize the occurrence of various events even if his mobile phone is in the user's pocket. Outputs informing about the occurrence of an event may be also provided via the display unit 151 or the audio output module 152. The display unit 151 and the audio output module 152 may be classified as a part of the alarm unit 153.

The haptic module 154 generates various tactile effects the user may feel. A typical example of the tactile effects generated by the haptic module 154 is vibration. The strength and pattern of the haptic module 154 can be controlled. For example, different vibrations may be combined to be outputted or sequentially outputted.

Besides vibration, the haptic module 154 may generate various other tactile effects such as an effect by stimulation such as a pin arrangement vertically moving with respect to a contact skin, a spray force or suction force of air through a jet orifice or a suction opening, a contact on the skin, a contact of an electrode, electrostatic force, etc., an effect by reproducing the sense of cold and warmth using an element that can absorb or generate heat.

The haptic module 154 may be implemented to allow the user to feel a tactile effect through a muscle sensation such as user's fingers or arm, as well as transferring the tactile effect through a direct contact. Two or more haptic modules 154 may be provided according to the configuration of the terminal 100.

The memory 160 may store software programs used for the processing and controlling operations performed by the controller 180, or may temporarily store data (e.g., a phonebook, messages, still images, video, etc.) that are inputted or outputted. In addition, the memory 160 may store data regarding various patterns of vibrations and audio signals outputted when a touch is inputted to the touch screen.

The memory 160 may include at least one type of storage medium including a Flash memory, a hard disk, a multimedia card micro type, a card-type memory (e.g., SD or DX memory, etc), a Random Access Memory (RAM), a Static Random Access Memory (SRAM), a Read-Only Memory (ROM), an Electrically Erasable Programmable Read-Only Memory (EEPROM), a Programmable Read-Only memory (PROM), a magnetic memory, a magnetic disk, and an optical disk. Also, the terminal 100 may be operated in relation to a web storage device that performs the storage function of the memory 160 over the Internet.

The interface unit 170 serves as an interface with every external device connected with the terminal 100. For example, the external devices may transmit data to an external device, receives and transmits power to each element of the terminal 100, or transmits internal data of the terminal 100 to an external device. For example, the interface unit 170 may include wired or wireless headset ports, external power supply ports, wired or wireless data ports, memory card ports, ports for connecting a device having an identification module, audio input/output (I/O) ports, video I/O ports, earphone ports, or the like.

The identification module may be a chip that stores various information for authenticating the authority of using the terminal 100 and may include a user identity module (UIM), a subscriber identity module (SIM) a universal subscriber identity module (USIM), and the like. In addition, the device having the identification module (referred to as 'identifying device', hereinafter) may take the form of a smart card. Accordingly, the identifying device may be connected with the terminal 100 via a port.

When the terminal 100 is connected with an external cradle, the interface unit 170 may serve as a passage to allow power from the cradle to be supplied therethrough to the terminal 100 or may serve as a passage to allow various command signals inputted by the user from the cradle to be transferred to the terminal therethrough. Various command signals or power inputted from the cradle may operate as signals for recognizing that the terminal is properly mounted on the cradle.

The controller 180 typically controls the general operations of the terminal. For example, the controller 180 performs controlling and processing associated with voice calls, data communications, video calls, and the like. The controller 180 may include a multimedia module 182 for reproducing multimedia data. The multimedia module 182 may be configured within the controller 180 or may be configured to be separated from the controller 180.

The controller 180 may perform a pattern recognition processing to recognize a handwriting input or a picture drawing input performed on the touch screen as characters or images, respectively.

Also, when a state of the terminal satisfies pre-set conditions, the controller 180 may execute a locked state for limiting an input of a control command of the user with respect to applications. Also, in a locked state, the controller may control a locked screen displayed on the locked state based on a touch input sensed through the display unit.

The power supply unit 190 receives external power or internal power and supplies appropriate power required for operating respective elements and components under the control of the controller 180.

Various embodiments described herein may be implemented in a computer-readable or its similar medium using, for example, software, hardware, or any combination thereof.

For hardware implementation, the embodiments described herein may be implemented by using at least one of application specific integrated circuits (ASICs), digital signal processors (DSPs), digital signal processing devices (DSPDs), programmable logic devices (PLDs), field programmable gate arrays (FPGAs), processors, controllers, micro-controllers, microprocessors, electronic units designed to perform the functions described herein. In some cases, such embodiments may be implemented by the controller 180 itself.

For software implementation, the embodiments such as procedures or functions described herein may be implemented by separate software modules. Each software module may perform one or more functions or operations described herein.

Software codes can be implemented by a software application written in any suitable programming language. The software codes may be stored in the memory 160 and executed by the controller 180.

Figure 2A:
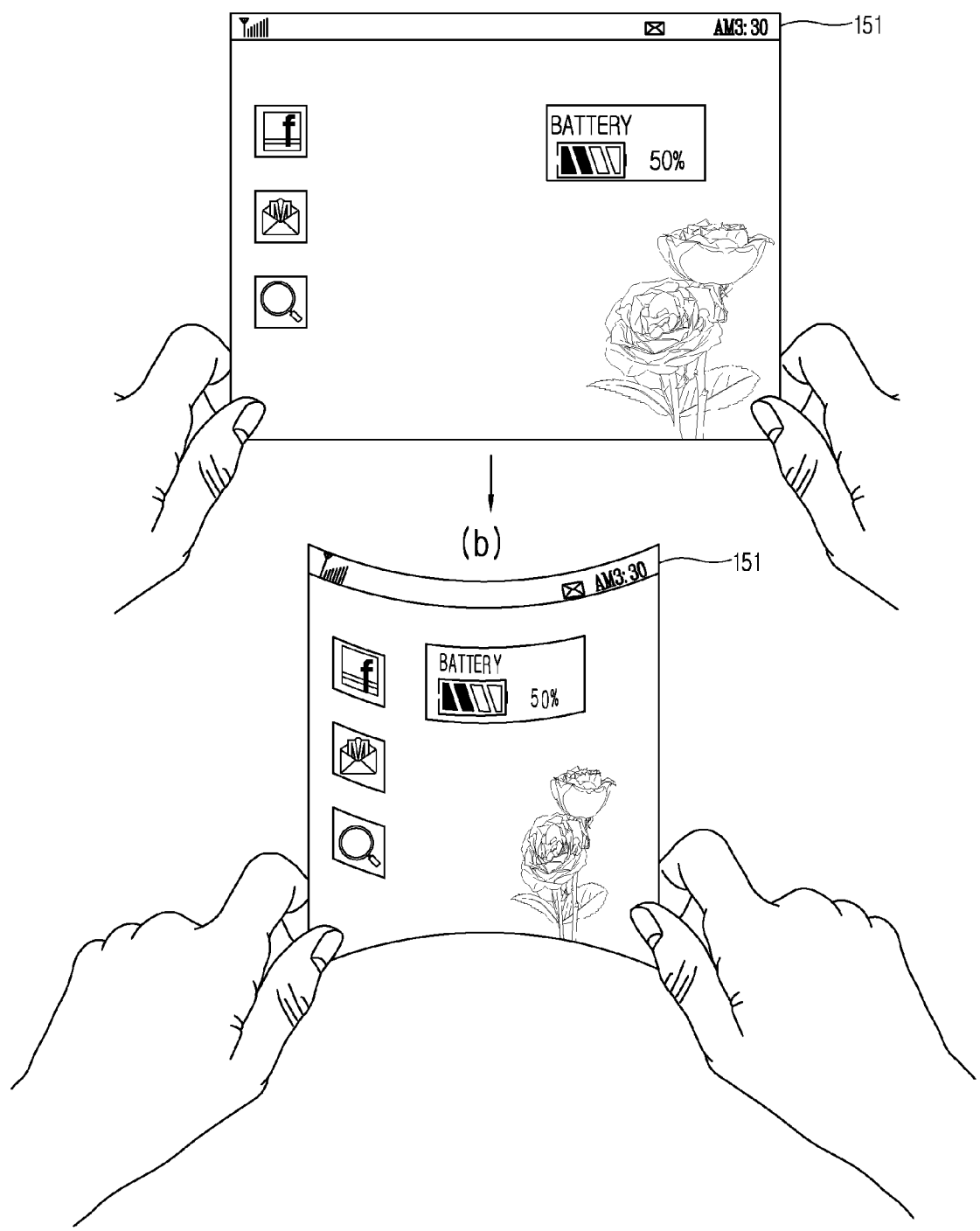
FIGS. 2A, 2B, and 2C are conceptual views illustrating a flexible display unit included in a terminal according to an embodiment of the present invention.

Meanwhile, in the present embodiment, information process in the terminal 100 may be displayed by using a flexible display. Hereinafter, a flexible display unit will be described in detail with reference to the accompanying drawings. FIGS. 2A and 2C are conceptual views illustrating a flexible display unit included in a terminal according to an embodiment of the present invention.

As illustrated in (a) and (b) of FIG. 2A, a flexible display unit 151 may include a display that can be bowable, bendable, foldable, or rollable by force applied from the outside. Here, the flexible display unit 151 may include a general flexible display and electronic paper.

Here, the general flexible display refers to a display which can be bowable, bendable, foldable, or rollable, like paper, while maintaining display characteristics of an existing flat panel display, and which is fabricated on a thin, flexible substrate, and is light and robust, and not broken.

Also, electronic paper is a display technique employing the characteristics of general ink, which is different from a general flat panel display, in that it uses reflected light. Electronic paper may change figures or characters by using electrophoresis using twist balls or capsules.

Meanwhile, the flexible display unit 151 includes the sensing unit 181 (please see FIG. 1) formed thereon, so it can sense bowing information regarding the flexible display unit 151. In the present disclosure, the term 'bowing' may include all the meanings of 'bending', 'rolling', and 'folding'.

The sensing unit 181 may be entirely or partially disposed on the flexible display unit 151, and may sense user's finger regarding the flexible display unit 151. Here, the bowing information of the flexible display unit 151 may include a direction in which the flexible display unit 151 is bowed, a degree at which the flexible display unit 151 is bowed, a position in which the flexible display unit 151 is bowed, a time at which the flexible display unit 151 is bowed, acceleration at which bowed flexible display unit 151 is returned to its original state, and the like. Besides, the bowing information may include various other types of information that can be sensed as the flexible display unit is bowed.

Also, the controller 180 may generate a control signal for changing information displayed on the flexible display unit 151 or controlling a function of the terminal on the basis of the bowing information regarding the flexible display unit 151 sensed by the sensing unit 181.

For example, as illustrated in (a) and (b) of FIG. 2A, when the flexible display unit 151 is bowed by external force, a screen image displayed on the flexible display unit 151 may be realigned, separated, or synthesized according to a direction in which the flexible display unit 151 is bowed, an angle at which the flexible display unit 151 is bowed, and returning acceleration at which the flexible display unit 151 is returned to its original state.

For example, as illustrated in (a) and (b) of FIG. 2A, when the flexible display unit 151 is inwardly bowed by external force, screen images displayed on the flexible display unit 151 may be displayed to be close to each other. Also, conversely, when the flexible display unit 151 is outwardly bowed by external force, the screen images displayed on the flexible display unit 151 may be displayed to be separated from each other.

Also, besides the methods discussed above, the controller 180 may variously control the method of displaying information on the flexible display unit 151 according to the bowing of the flexible display unit 151, such that the user may accurately recognize information displayed on the flexible display unit 151.

Figure 2B:
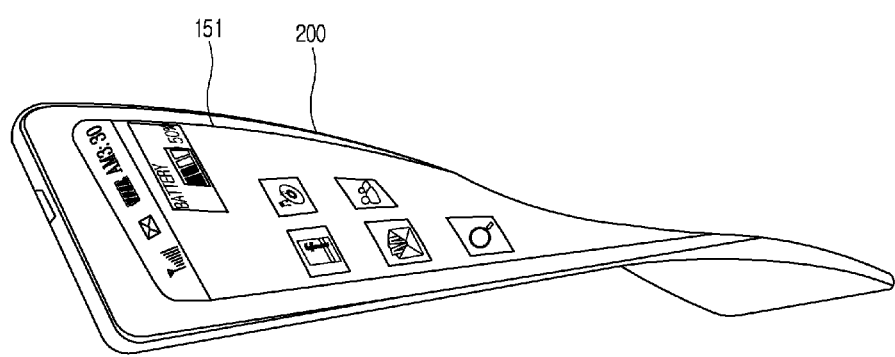
Figure 2C:
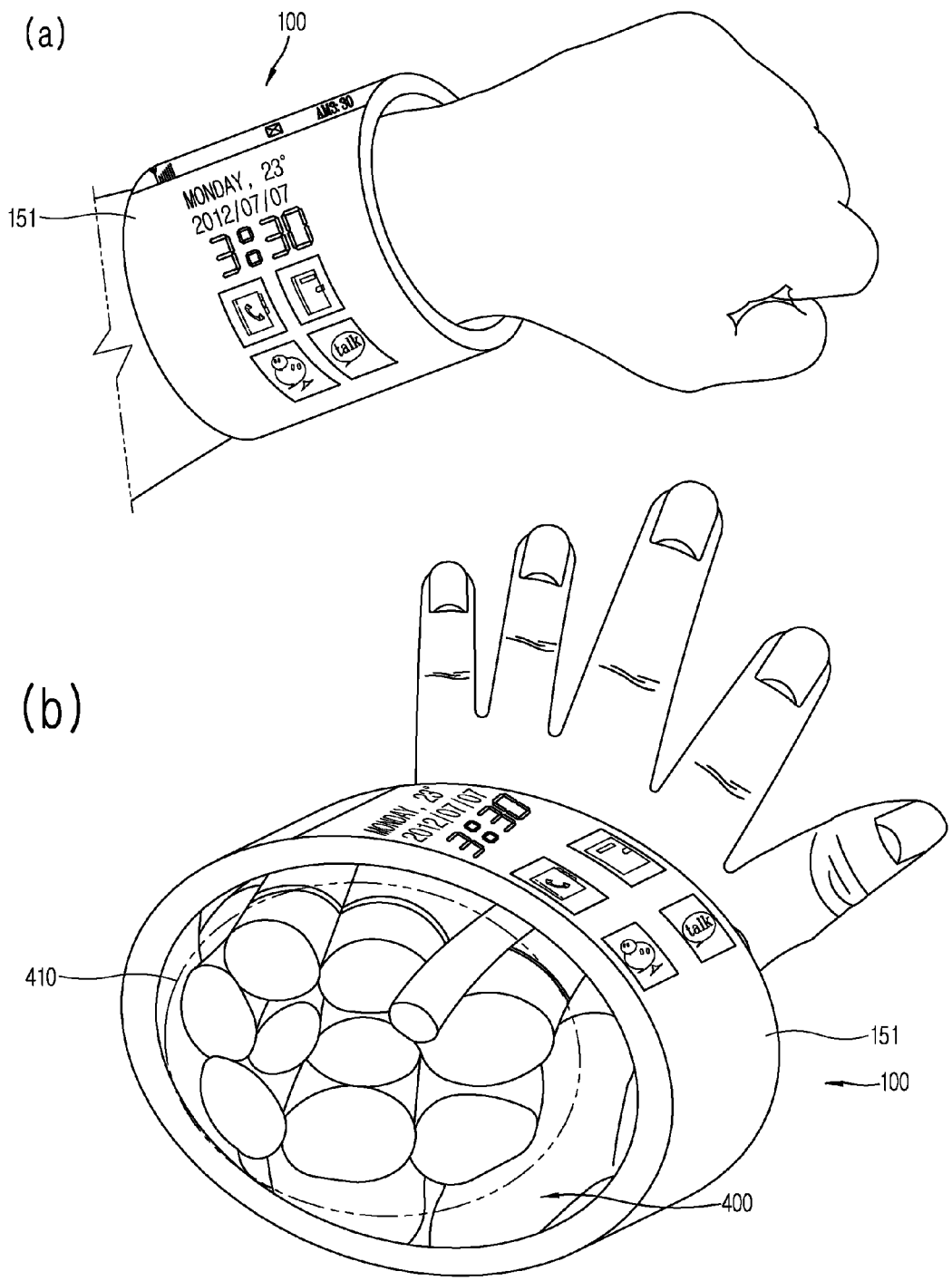

Meanwhile, as illustrated in FIG. 2B, the terminal including the flexible display unit 151 according to an embodiment of the present invention may include a case 200 surrounding the flexible display unit 151. Also, in consideration of the characteristics of the flexible display unit 151, the case 200 may be configured to be bowed together with the flexible display unit 151 by external force.

Meanwhile, as mentioned above, in response to bowing information of the flexible display unit 151, the controller 180 may generate a control signal related to a function of the terminal according to an embodiment of the present invention.

Also, as illustrated in (a) of FIG. 2C, the terminal according to an embodiment of the present invention may be implemented in the form of wrapping a user's wrist.

Also, as illustrated in (b) of FIG. 2C, in the terminal according to an embodiment of the present invention, the sensing unit 140 is disposed in a surface of the terminal in which the flexible display unit 151 is in contact with the wrist, such that movements of a plurality of tendons passing through the wrist may be sensed by the sensing unit 140. In this case, the sensing unit 140 may serve as a finger movement detection unit. Namely, the sensing unit 140 may sense movements of tendons according to a movement of a finger and transfer the sensed information to the controller 180. Also, the controller 180 may process a function matched to the movement of the user's finger on the basis of the sensed information from the sensing unit 140.

Meanwhile, referring to movements of tendons according to a movement of a user's finger, user's finger flexor tendons administering a movement of user's fingers exist in a carpal tunnel 410 within the wrist 410. Nine tendons and one nerve exist in the finger flexor tendons, and when a user's finger moves, the nine tendons included in the user's finger flexor tendons move in various combinations. The sensing unit 140 may sense a shape of the tendons altered according to a movement of a user's finger or wrist, and the controller 180 may determine a gesture made by fingers based on the sensed information.

In this case, the memory 160 may have shape information regarding the tendons matched to the different finger gestures, stored therein.

Meanwhile, the sensing unit 180 may sense a change in grasping power and a movement speed of a finger, as well as a shape of the tendons altered according to a movement of a user's finger.

Namely, the sensing unit 180 may sense movement characteristics of tendons, and here, the movement characteristics may be at least one of a shape (or a gesture), a movement speed of a finger, a movement direction of a write, a movement speed of a wrist, and a change in grasping power.

Meanwhile, as described above, since the terminal according to an embodiment of the present invention wraps the wrist through the display unit 151, a movement and a shape of tendons can be sensed through the sensing unit 140.

Hereinafter, a method for executing a function matched in advance to sensed movement characteristics on the basis of movement characteristics of tendons sensed through the forgoing method will be described in detail with reference to the accompanying drawings.

Figure 3:
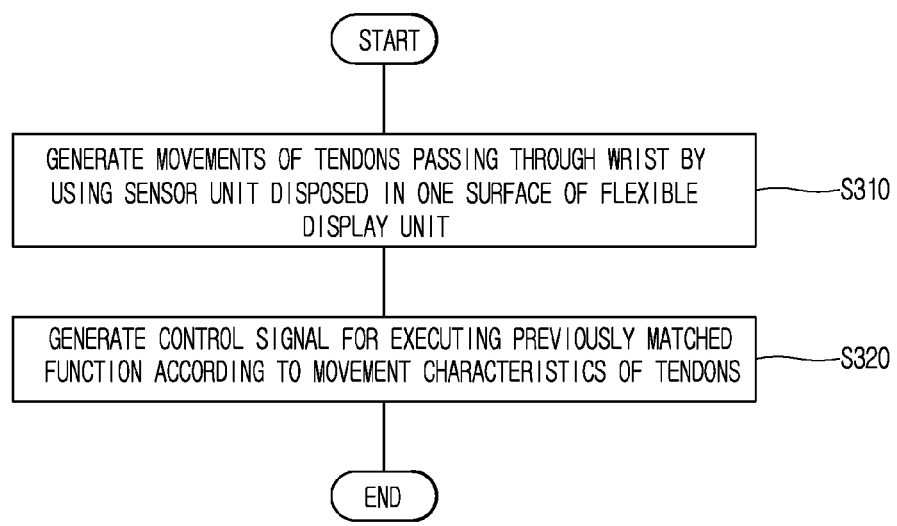
FIG. 3 is a flow chart illustrating a method for controlling a control signal on the basis of information regarding movement characteristics of tendons in the terminal according to an embodiment of the present invention.

FIG. 3 is a flow chart illustrating a control method for generating a control signal by using the flexible display unit in the terminal according to an embodiment of the present invention. FIGS. 4A and 4B are conceptual views illustrating the control method of FIG. 3.

First, the sensing unit 140 (please see FIG. 1 and (b) of FIG. 2C) senses movements of tendons passing through the wrist (S310). Here, the sensing unit 140 is disposed in a portion in which the flexible display unit 151 meets the wrist. Also, tendons as sensing targets of the sensing unit 140 are tendons included in the carpel tunnel 410) as mentioned above with reference to (b) of FIG. 2C.

In step S310, when movements of the tendons are sensed by the sensing unit 310, the controller 180 generates a control signal for executing a function previously matched to sensed movement characteristics of the tendons (S320).

Here, as discussed above, the movement characteristics of the tendons may be at least one of a shape (or gesture) of a finger, a movement speed of a finger, a movement direction of a finger, a movement speed of a wrist, and a change in grasping power. Also, such movement characteristics may be variously changed according to a movement of a finger or a wrist. For example, movement characteristics when five fingers are spread out and those when five fingers are cupped are different. Namely, movements and shapes of the tendons differ according to movements of the fingers.

Namely, the controller 180 generates a control signal for executing different functions corresponding to different movement characteristics of the tendons. For example, when a shape (or a gesture) of a user's finger corresponds to a pre-set first shape, the controller 180 may generate a first control signal corresponding to a first function matched to the first shape. Also, when a shape of the user's finger corresponds to a pre-set second shape, the controller 180 may generate a second control signal corresponding to a second function matched to the second shape.

Also, here, the control signal for executing a 'previously matched function' is a control signal for controlling the terminal according to the present invention. Thus, in the terminal according to an embodiment of the present invention, a function according to a control signal generated on the basis of sensed movement characteristics of the tendons may be executed. Thus, by simply sensing movements of tendons or a shape according to a movement, various different functions may be executed in the terminal according to an embodiment of the present invention. Also, functions matched to movement characteristics of different fingers may be set according to a user selection or an initial setting, respectively.

Examples of executing different functions according to shapes of different fingers will be described. As illustrated in (a) of FIG. 4A and (a) of FIG. 4B, when fingers have different shapes, different functions are executed in the terminal as illustrated in (b) of FIG. 4A and (b) of FIG. 4B.

For example, when a first finger 421 and a fifth finger 425 are spread out while the other remaining second, third, and fourth fingers are cupped as illustrated in (a) of FIG. 4A, the controller 180 generates a control signal corresponding to a 'cal' related function matched to the finger shape (or gesture) as illustrated. As a result, as illustrated in (b) of FIG. 4A, an execution screen executing the 'call' related function may be output to the flexible display unit 151.

In another example, when the second finger 422 and the third finger 423 are spread out and the other remaining first, fourth, and fifth fingers are cupped, the controller 180 generates a control signal corresponding to a 'camera' function matched to the finger shape (or gesture) as illustrated. As a result, as illustrated in (b) of FIG. 4, the camera 121 or 121' (please see FIGS. 2A and 2B) may be activated, and an image input through the camera may be output to the flexible display unit 151.

Meanwhile, besides the examples described with reference to FIGS. 4A and 4B, the controller 180 may execute a pre-set function on the basis of a dynamic movement of a finger, a movement speed of a finger, a change in grasping power, and a movement and a speed of a wrist, or a speed.

Figure 5B:
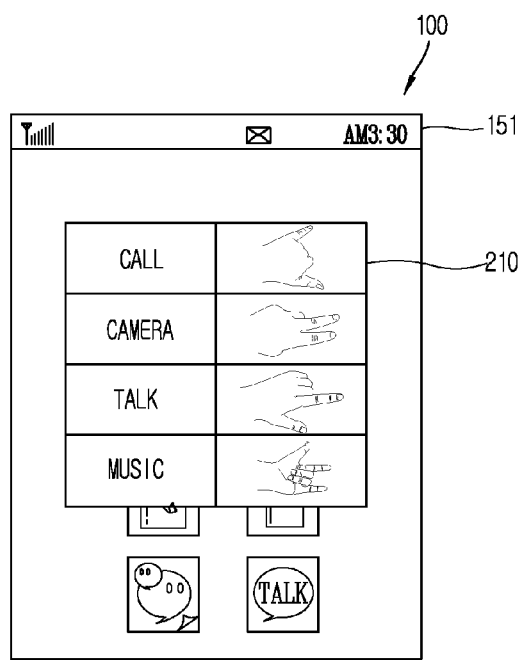

As described above, the terminal may execute different functions according to different finger gestures. Thus, the user may execute a desired function even with a movement of his finger or wrist, without applying a control command through a touch, or the like, to the flexible display unit Hereinafter, a method for executing a function corresponding to a user's finger or wrist only when a starting gesture is sensed will be described with reference to the accompanying drawings. FIGS. 5A and 5B are conceptual views illustrating a method for receiving a preparatory movement in the terminal according to an embodiment of the present invention.

In the terminal according to an embodiment of the present invention, in a case in which the user simply moves his finger or hand, rather than moving the finger or the wrist in order to generate a control signal, a generation of an erroneous control signal can be prevented. Namely, in the terminal according to an embodiment of the present invention, in a case in which a pre-set starting gesture is sensed, the controller 180 may execute a function corresponding to movement characteristics of tendons sensed through the sensing unit 180.

Here, the pre-set starting gesture may be based on a user setting or may correspond to initial setting information.

For example, in a case in which the pre-set starting gesture is a gesture of moving the second finger 422 in a certain direction one time and the second finger is moved to correspond to the pre-set starting gesture as illustrated in (a) of FIG. 5A, the controller 180 may generate a control signal related to a function corresponding to the movement characteristics of the tendons, after the starting gesture is sensed.

Also, in order to inform the user that the starting gesture has been sensed, as illustrated in (b) of FIG. 5A, the controller 180 may output guidance information to the flexible display unit 151. Also, the guidance information may be output through an audible or tactile method such as a voice, vibration, or the like, in addition to a visual method illustrated in (b) of FIG. 5A.

Also, after the starting gesture is sensed, when a pre-set time has lapsed or in a case in which a pre-set finish gesture is sensed, the controller may not execute a function of the sensed movements of the tendons although movements of tendons are sensed by the sensing unit 140.

Also, as illustrated in FIG. 5B, the controller may output guidance information 210 related to a function matched to each of different movement characteristics according to different movements of the tendons, to the flexible display unit 151.

As described above, in the terminal according to an embodiment of the present invention, when a starting gesture is sensed, a function corresponding to movement characteristics of tendons is executed, thus preventing execution of an unnecessary function against a user intention.

Hereinafter, methods for controlling various functions according to movement characteristics of tendons and directions in which a wrist faces will be described through specific embodiments. FIGS. 6A, 6B, 6C, 7A, 7B, 8A, and 8B are conceptual views illustrating methods for generating various control signals according to different motion characteristics in the terminal according to an embodiment of the present invention.

For example, a method for controlling a camera-related function according to movement characteristics of tendons in a state in which a camera function is activated will be described. In the terminal according to an embodiment of the present invention, when movements of tendons according to a movement of a user's finger are sensed, the controller 180 may be able to estimate a distance between at least two fingers on the basis of sensed information.

In this manner, when the distance between the fingers is estimated, the controller 180 may generate a control signal on the basis of estimated distance information between the fingers.

Figure 6B:
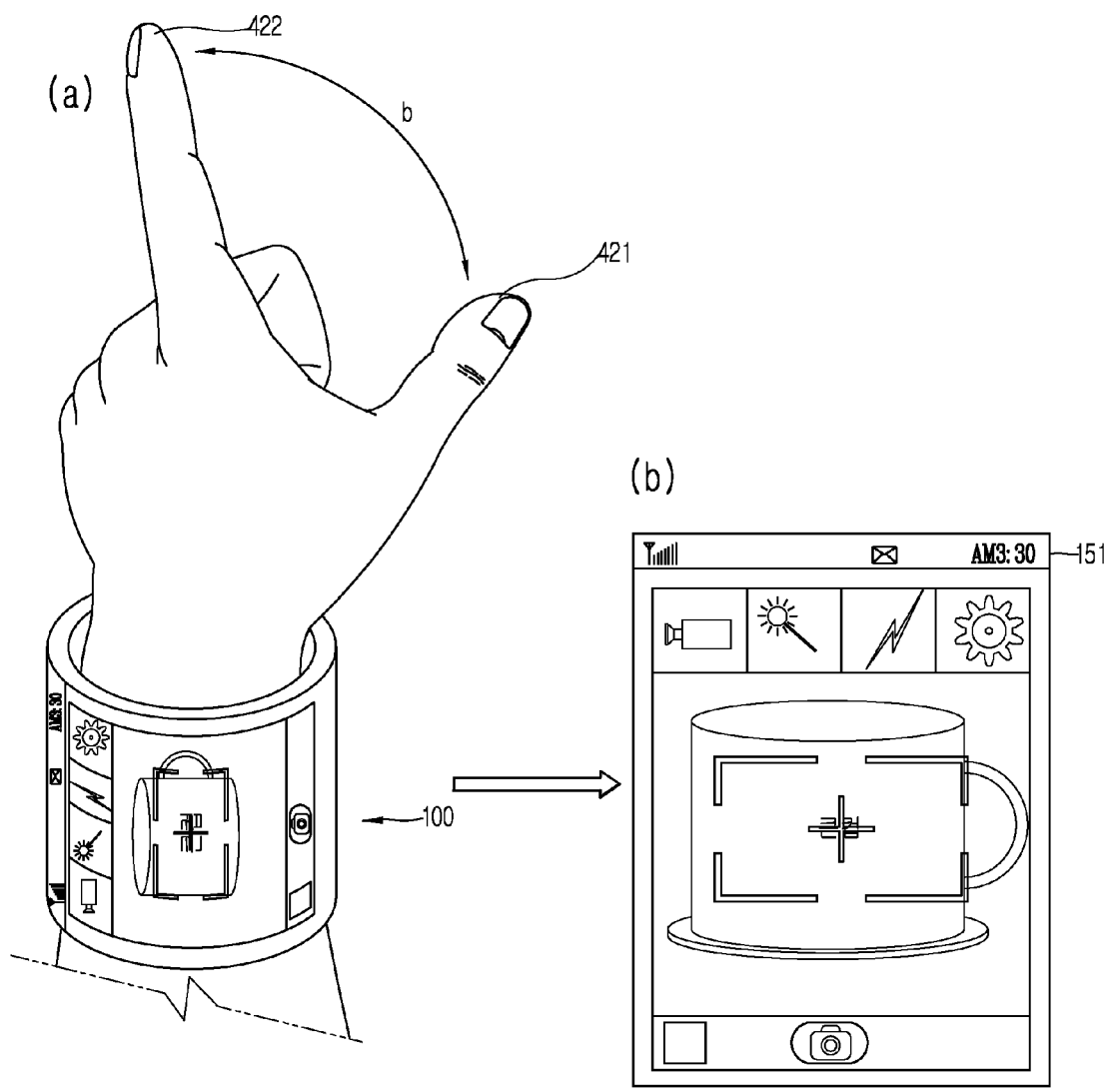
Figure 6C:
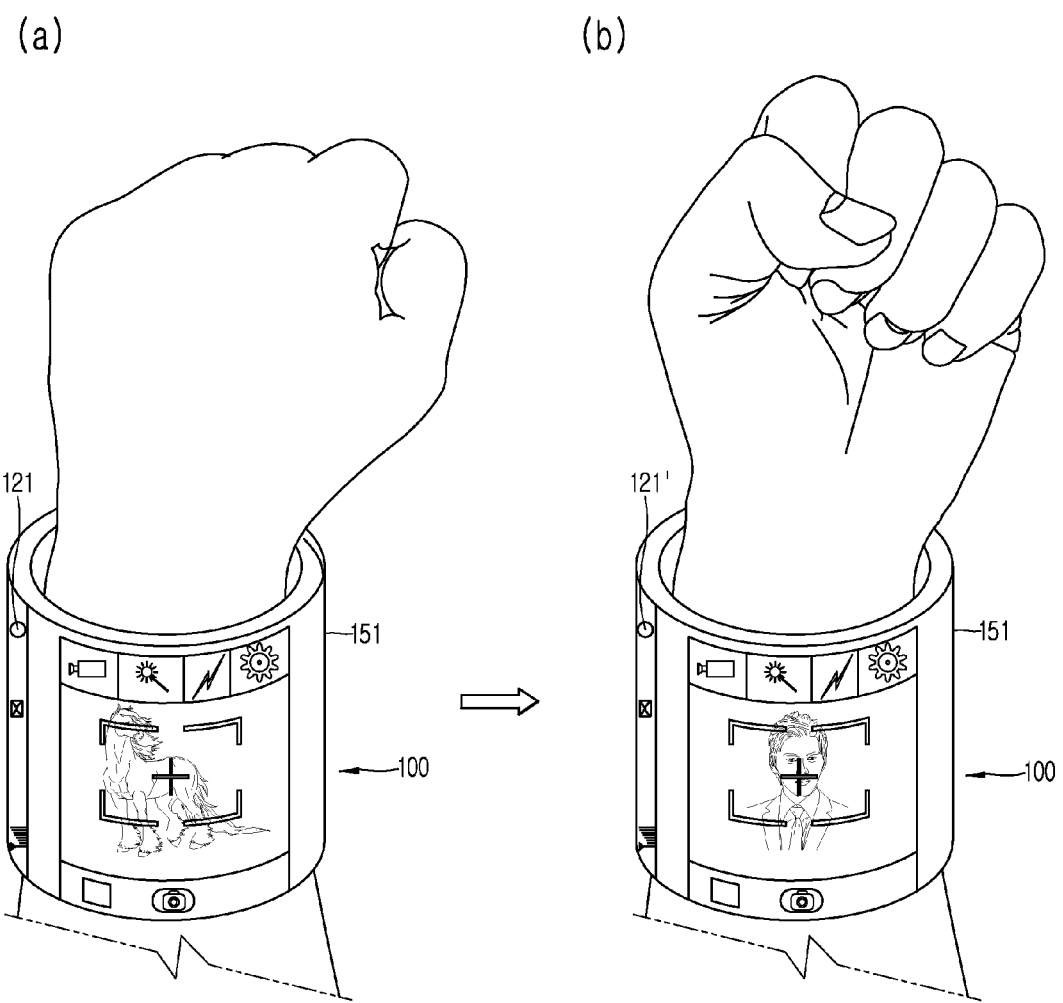

For example, as illustrated in FIGS. 6A and 6B, the controller 180 may adjust a magnification of a camera on the basis of a distance between the different fingers. Namely, the controller 180 may control a zoom-in or zoom-out function on the basis of a distance between the different fingers.

When an estimated distance 'a' between first and second fingers 421 and 422 is smaller than a reference distance, the controller 180 may execute the zoom-out function as illustrated in (a) and (b) of FIG. 6A. Also, when the estimated distance 'a' between the first and second fingers 421 and 422 is greater than the reference distance, the controller 180 may execute the zoom-in function as illustrated in (a) and (b) of FIG. 6B. Also, when the zoom-in or zoom-out function is executed, the controller 180 may control magnifications thereof differently according to the distance between the fingers.

Meanwhile, the terminal according to an embodiment f the present invention includes a plurality of cameras disposed in different positions, and the controller 180 may control at least one of the plurality of cameras such that the corresponding camera, among the plurality of cameras, is activated according to a direction in which the wrist faces.

For example, a case in which a first camera 121, among the plurality of cameras, is disposed in a surface corresponding to the back of a hand and a second camera 121' is disposed in a surface corresponding to a palm will be described. In this case, the controller 180 may sense the direction in which the back of the hand (or the palm) faces through a motion sensor (not shown) included in the sensor unit 140. Here, the motion sensor 141 may be installed within the terminal 100 and may recognize a movement or a position of the terminal 100. The motion sensor may include a geomagnetic sensor, an accelerometer, a gyro sensor, and the like.

According to the sensing results obtained through the sensor unit 140, when the back of the hand faces the user, the controller 180 may activate the second camera 121', and when the palm faces the user, the controller 180 may activate the first camera 121, thus receiving different images through the cameras.

Meanwhile, in this case, the controller 180 may control a region in which information (e.g., an image input through the cameras) is displayed of the flexible display unit 151 according to a direction in which the back of the hand or the palm faces the user. Namely, the controller 10 may change a region in which information is displayed on the flexible display unit 151 according to a direction of the user's eyes.

Also, although not shown, the controller 180 may control various functions related to the cameras on the basis of movement characteristics of the tendons according to a movement of the user's wrist or finger. For example, the controller 180 may control variously multiple functions related to the cameras such as the number of continuously photographed shots, a photograph command, adjustment of brightness, adjustment of light and shade, and the like, according to a user selection.

Figure 7A:
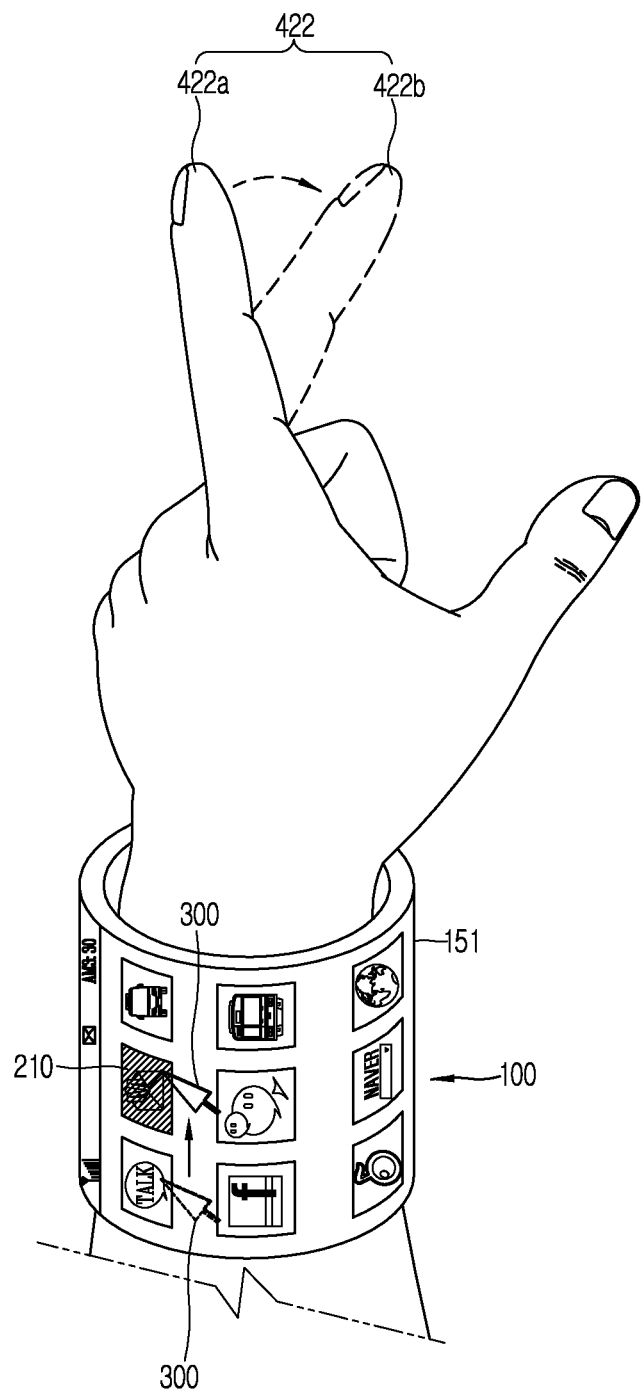

In another example, a method for selecting at least one of selection target items displayed on the flexible display unit 151, on the basis of movement characteristics of tendons will be described. For example, as illustrated in FIG. 7A, the controller 180 may move a graphic object (or a touch pointer) 300 displayed on the flexible display unit 151 according to a movement of a user's finger 422 from 422*a* to 422*b*.

Also, as illustrated in (a) of FIG. 7B, as at least two fingers 421 and 422 meet, the controller 180 may control the flexible display unit 151 such that an item 210 displayed. When the item 210 displayed in the portion where the touch pointer 300 is positioned is selected as illustrated in (a) of FIG. 7B, information corresponding to the selected item 210 may be output to the flexible display unit 151 as illustrated in (b) of FIG. 7B.

Hereinafter, a method for controlling a function in an application related to music or video play (or reproduction) on the basis of movements of tendons according to a movement of a user's wrist or finger will be described.

Figure 8A:
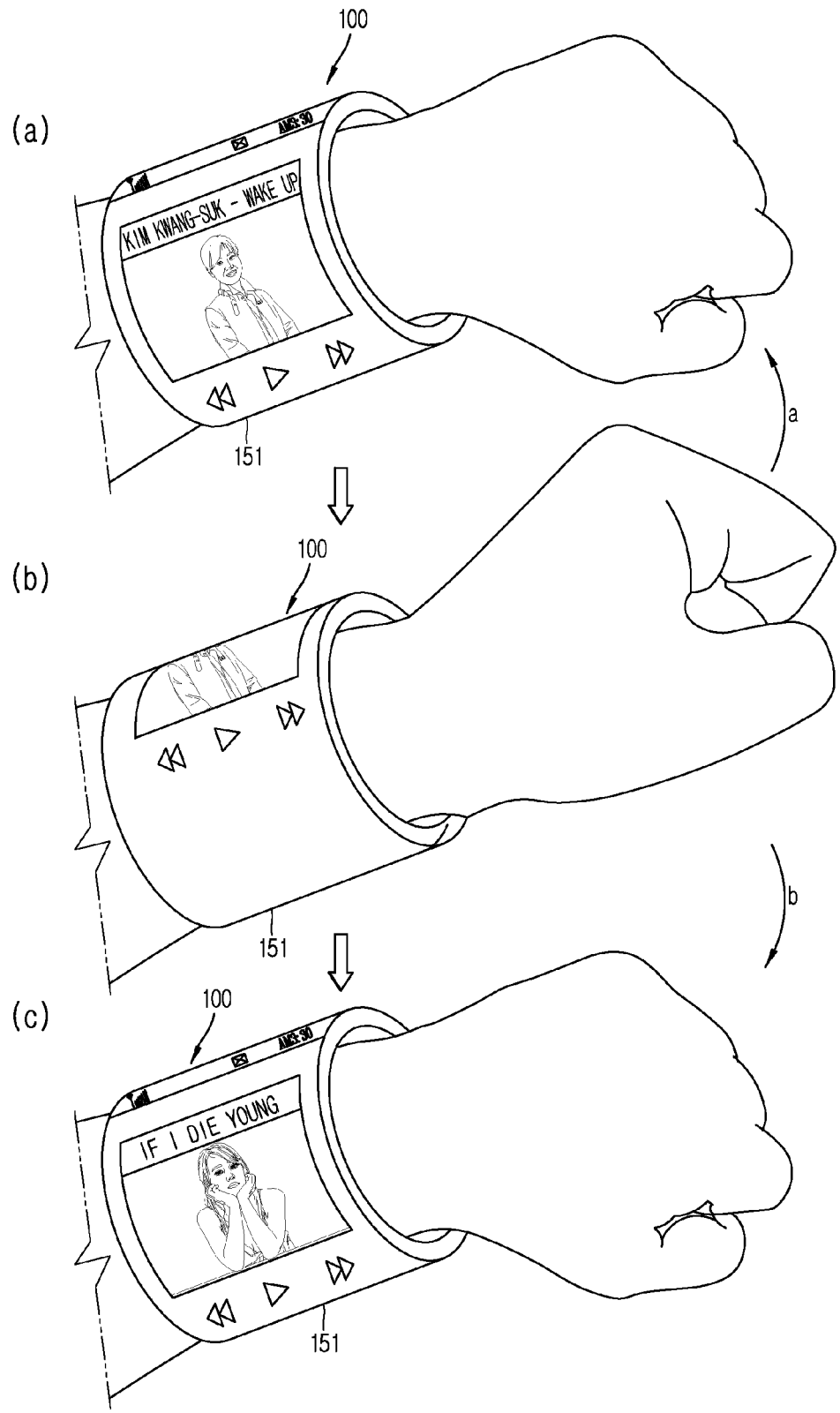

For example, as illustrated in (a), (b), and (c) of FIG. 8A, when the wrist rotates in a first direction (a) and is subsequently returned to its original direction (b), the controller 180 may play (or reproduce) a second piece of music next to a first piece of music being currently played, from a play list.

Also, the controller 180 may determine whether to play a subsequent piece of music of a current piece of music being played, or whether to play a previous piece of music of the current piece of music.

Figure 8B:
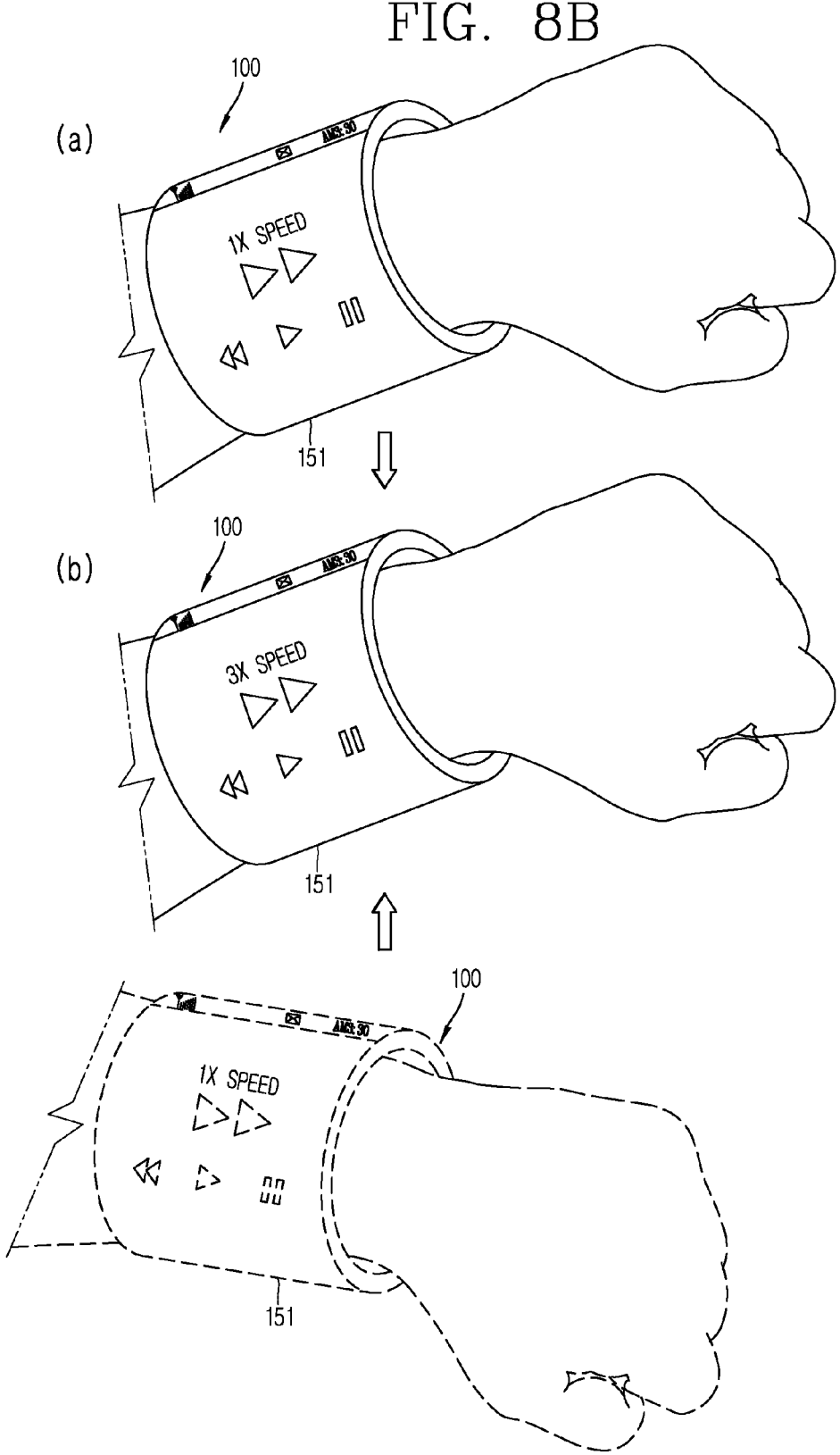

Also, as illustrated in (a) of FIG. 8B, in an audio or video-related application, while a currently played file is being searched at 1× speed, when the write moves in a predetermined direction as illustrated (b) of FIG. 8B, the search speed may be increased to 3× speed.

Figure 9A:
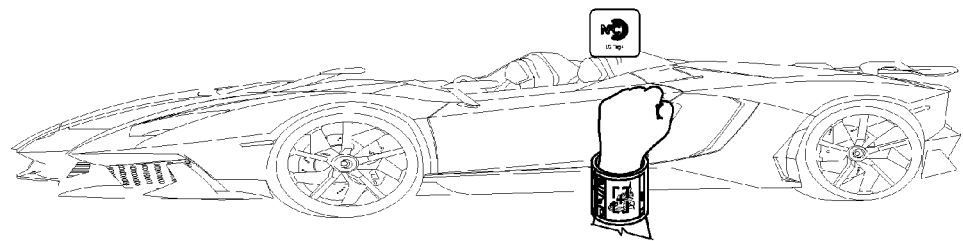

In another example, as illustrate din FIG. 9A, in a case in which a locking device such as a locking device of a vehicle or a door lock is released through NFC (Near Field Communication) performed by the wireless communication unit 110, only when pre-set movement characteristics of tendons are sensed, the controller 180 may transmit a signal for unlocking the locking device to the locking device.

Thus, in this case, only when the disposition of the tendons specific to the user is sensed or only when movements of tendons in a pre-set pattern are sensed, the controller 180 unlocks the locking device, whereby the user can strengthen security of the locking device.

In another example, as illustrated in (a), (b), and (c) of FIG. 9B, in the locked state in which a control command of an application is limited, when pre-set movement characteristics of tendons are sensed, the controller 180 may change the locked state into an unlocked state.

Here, the locked state is a state in which an input of a user control command with respect to applications included in the terminal is limited. This is to prevent inputting of a control command not intended by the user in the terminal including a touch screen (or a display unit configured as a touch screen, or a flexible display unit 151) to thus prevent activation of deactivation of functions and applications of the terminal. Thus, in the locked state, a user input of a control command performed through the touch screen (or the display unit 151) and any other user input unit 130 may be limited to a pre-set range.

Meanwhile, in the locked state, although a user input of a control command is limited, functions of the terminal and operations of applications of the terminal, which have been operated before the terminal enters the locked state, may be continuously executed.

The unlocked state refers to a state in which a user input of a control command with respect to the terminal is not limited. Thus, in the unlocked state, functions and applications of the terminal are activated or deactivated according to a control command input by the user through the touch screen (or the display unit 151) or the user input unit 130.

Here, the locked state may be executed when a user input with respect to the touch screen (or the display unit 151) and any other user input unit 130 provided in the terminal is not sensed for a pre-set period of time. The pre-set period of time may be changed according to a user setting. Also, the locked state may be executed when the user presses a special key (e.g., a hold key) provided in the terminal previously set for the locked state.

In this manner, the user may change a locked state into an unlocked state only with a movement of the user's wrist or finger, in addition to the method of changing the locked state into the unlocked state by applying a touch to the flexible display unit of the terminal according to an embodiment of the present invention. Thus, even when the user cannot use both hands, he or she may unlock the locked state.

Meanwhile, in the terminal according to an embodiment of the present invention, the controller 180 may control differently a size of a region in which information is displayed according to where the flexible display unit 151 is positioned in the user's wrist.

As discussed above, information may be displayed in the entire region of the flexible display unit 151 bowed to wrap the user's wrist. However, substantially, the user may view only information displayed in a portion of the flexible display unit 151 according to a direction in which the back of the hand (or the palm) faces.

Thus, the controller 180 according to an embodiment of the present invention may recognize a direction in which the back of the hand faces through a camera sensor or the motion sensor as mentioned above, and control a region in which information is displayed according to the recognized direction. For example, when the back of the user's hand faces the user's eyes, the controller 180 may display information in a region of the flexible display unit 151 corresponding to the direction of the back of the user's hand.

Figure 10A:
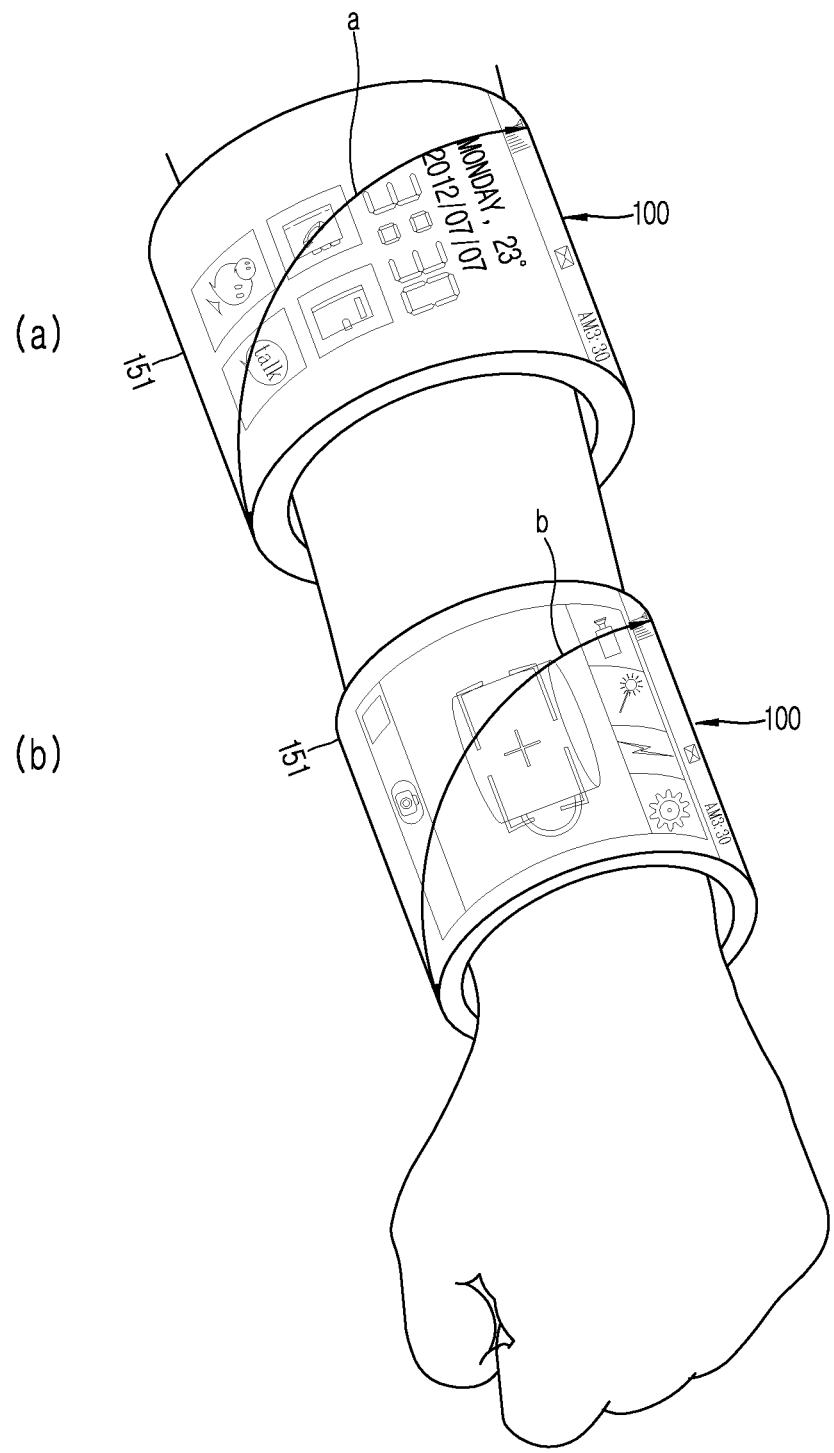

Also, as illustrated in FIG. 10A, the controller 180 may control a size of the region in which information is displayed according to an area of the flexible display unit 151 in contact with the user's wrist. For example, the sensing unit 140 may sense an area thereof in contact with the user's wrist. The controller 180 may determine a position of the flexible display unit 151 wrapping the user's wrist, on the basis of the sensed information as mentioned above. The controller 180 may control a size of the region in which information is displayed according to the determined position.

Thus, as illustrated, when the flexible display unit 151 is positioned to be closer to the user's body (user's elbow) than to the user's palm, an area in which the flexible display unit 151 is in contact is increased, so the controller 180 may control the size of the information display region when the flexible display unit 151 is in the position 'a', such that it is greater than that of the information display region when the flexible display unit 151 is in the position 'b'.

Meanwhile, tendons in the position 'a' exist deeper in the body than those in the position 'b', so the controller 180 may control the sensing unit 140 to have stronger sensitivity in the position 'a'.

Also, as illustrated in (a) and (b) of FIG. 10B, in a case in which the information display region of the flexible display unit 151 is changed on the basis of a direction of the user's eyes, the controller 180 may control the flexible display unit 151 to change an amount of information displayed thereon on the basis of a size of the changed information display region.

As discussed above, the terminal according to an embodiment of the present invention is able to effectively provide information to the user by changing a region in which information is displayed according to a position of the flexible display unit 151 and a direction of the user's eyes.

Meanwhile, as illustrated in FIG. 11, in the terminal according to an embodiment of the present invention, the user may directly set a function corresponding to a particular gesture. For example, as illustrated in (b) of FIG. 11, in a case in which a corresponding gesture is desired to be matched to a navigation function, when the navigation function is selected by the user, the controller 180 may output inducement information for receiving a gesture to be matched to the navigation function as illustrated in (c) of FIG. 11. Also, as illustrated in (c) and (d) of FIG. 11, when a particular gesture is recognized through the sensing unit 140, it may be matched to the navigation function.

Also, although not shown, in the terminal according to an embodiment of the present invention, besides the method of recognizing a particular gesture on the basis of a gesture directly made by the user, any one of previously stored gesture items may be selected by the user.

In this manner, in the terminal according to an embodiment of the present invention, the user may establish a user-tailored setting environment by directly selecting or inputting a gesture corresponding to a particular function.

Figure 12:
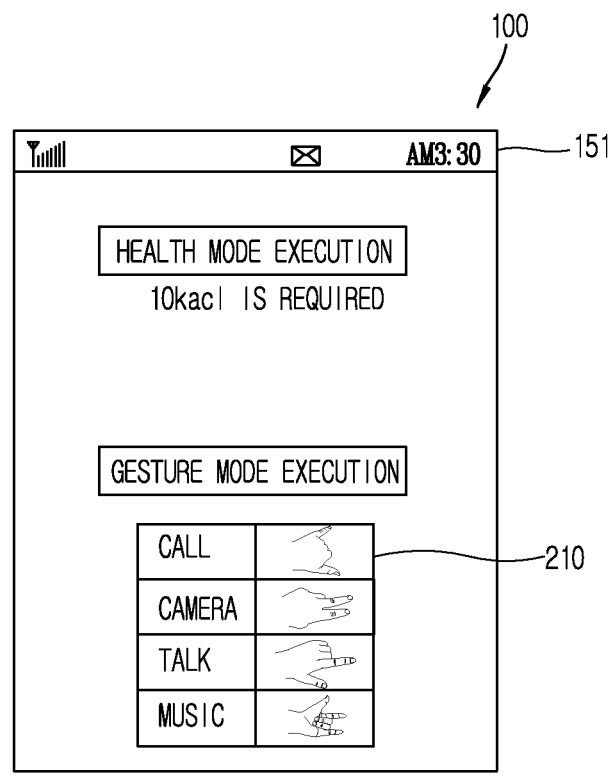
FIG. 12 is a conceptual view illustrating a method for performing a function using motion characteristics in the terminal according to an embodiment of the present invention.

Meanwhile, in the terminal according to an embodiment of the present invention, the user may activate a particular mode such as a 'health mode' to help the user's health by moving his finger or wrist. The health mode may be activated on the basis of a user selection. Thus, as illustrated in FIG. 12, in the state in which the health mode is activated, information regarding calories to be consumed and gesture information corresponding to each of particular functions are output to induce the user to move his finger or wrist.

As discussed above, in the terminal according to an embodiment of the present invention, functions of the terminal can be executed through a gesture according to a user movement and user health can be enhanced.

Also, in the terminal and the control method thereof according to an embodiment of the present invention, movements of the tendons passing through the user's wrist can be sensed by using the flexible display unit wrapping the user's wrist. Thus, the user may execute a function matched according to movement characteristics of tendons by simply moving his wrist or finger without having to apply a control command through a touch input, or the like, to the flexible display unit. Namely, in the terminal and the control method thereof according to an embodiment of the present invention, various functions can be executed by using one hand, rather than both hands, increasing user convenience.

Figure 13:
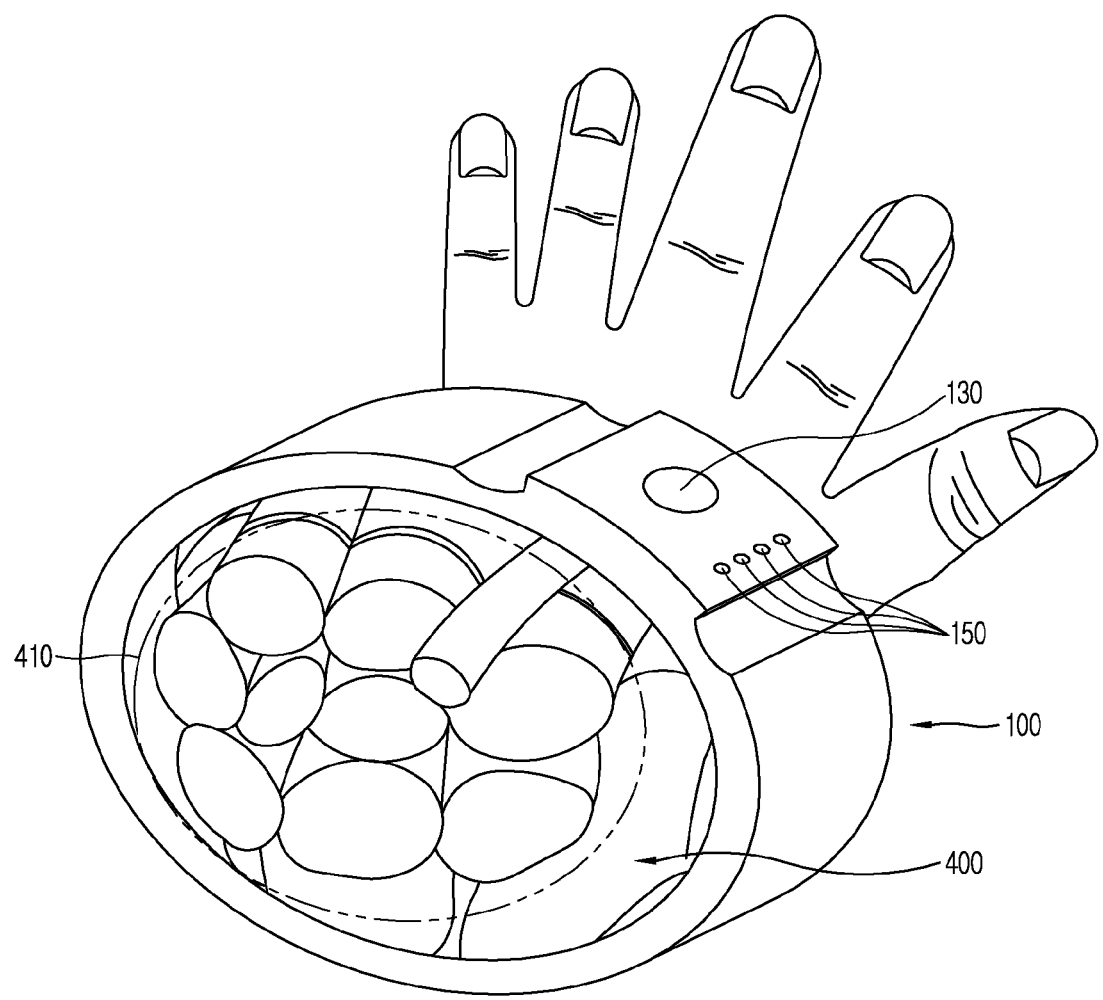
FIG. 13 is a conceptual view illustrating a terminal that transmits a control signal to an external device according to an embodiment of the present invention.

Meanwhile, in the present embodiment, the terminal 100 may be put on part of the user's body and generate a control signal for controlling an external device. Hereinafter, the terminal 100 which transmits a control signal to an external device will be described in detail with reference to the accompanying drawings. FIG. 13 is a conceptual view illustrating a terminal that transmits a control signal to an external device according to an embodiment of the present invention.

As illustrated in FIG. 13, the terminal 100 according to an embodiment of the present invention may be implemented such that a body thereof wraps a user's wrist.

Also, as illustrated in FIG. 2, in the terminal according to an embodiment of the present invention, the sensing unit 140 is disposed in a surface of the body of the terminal 100 in contact with the user's wrist, so that a plurality of tendons passing through the user's wrist and a movement of the user's wrist may be sensed by the sensing unit 140.

In this case, the sensing unit 140 may serve as a detection unit for detecting a movement of the user's finger. Namely, the sensing unit 140 may sense movements of tendons according to a movement of the user's finger, and transfer the sensed information to the controller 180. Also, the controller 180 may process a function matched to the movement of the user's finger on the basis of the sensed information from the sensing unit 140.

this case, the memory 160 may have shape information regarding the tendons matched to the different finger gestures, stored therein. Also, the memory 160 may store movement characteristics of tendons according to a movement of the user's wrist, stored therein.

Meanwhile, the sensing unit 140 may sense a change in grasping power, a movement speed and an angular velocity of the user's wrist, a movement of the user's wrist, and the like, as well as the shape of the tendons changed according to a movement of the user's finger. Namely, the sensing unit 140 may determine how the movement characteristics of the user's wrist and finger(s) are changed. For example, the sensing unit 140 may sense a state in which the user clenches his first to a state in which the user spreads out all the fingers, a state in which the user claps his hands, and a state in which the user hit fingers each other to make a sound, and the like.

Namely, the sensing unit may sense movement characteristics of the tendons, and here, the movement characteristics may be at least one of a shape (or gesture) of the user's fingers, a change in grasping power, a movement speed of the user's fingers, a movement direction of the user's wrist, a movement speed of the user's wrist, acceleration of the user's wrist, and an angular velocity of the user's wrist.

The terminal 100 may include the user input unit 130 and the output unit 150 formed on an outer circumferential surface of the body thereof.

For example, in the terminal 100 according to an embodiment of the present invention, the user input unit 130 may be a button for turning on or turning off power of the terminal 100. In another example, the user input unit 130 may be a button for preventing an erroneous generation of a control signal in case in which the user simply moves his fingers or hand. Namely, when a user input applied to the user input unit 130 is sensed, the sensing unit 140 is activated for a pre-set period of time. The controller 180 may generate a control signal corresponding to movement characteristics of tendons sensed by the activated sensing unit 140

The output unit 150 may output information regarding a power state of the power supply unit 190 or information regarding whether the sensing unit 140 is activated, by using a light emitting diode (LED).

Although not shown, a display unit may be provided in an outer circumferential surface of the body to output information regarding control of the terminal 100. For example, the display unit may output information regarding shapes of the user's fingers and information regarding control functions corresponding to the shapes. Here, the display unit may be a flexible display unit that can be bowed together with the body of the terminal 100.

Also, the wireless communication unit 110 (please see FIG. 1) transmitting a generated control signal to an external device may be provided in the body of the terminal 100. The external device may be a device that can be connected to the terminal 100 within a short range. When the external device is positioned in a pre-set region, it may be automatically connected to the terminal 100 or may be connected to the terminal 100 selectively according to a user input.

Figure 14:
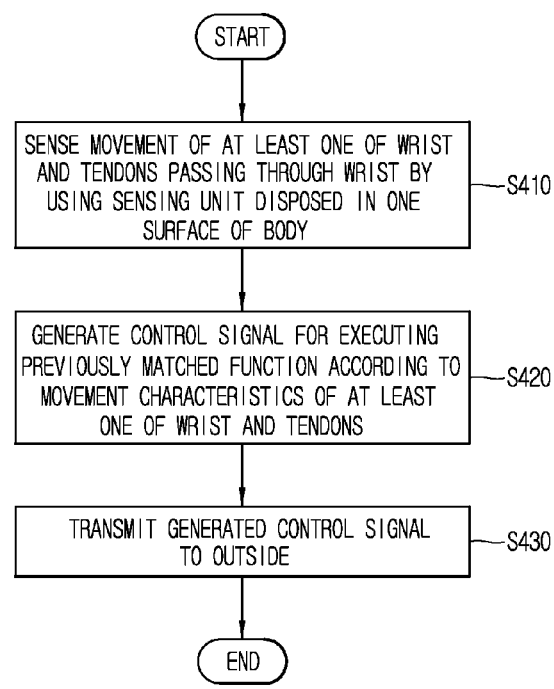
FIG. 14 is a flow chart illustrating a control method for controlling a control signal in the terminal according to an embodiment of the present invention.
Figure 15:
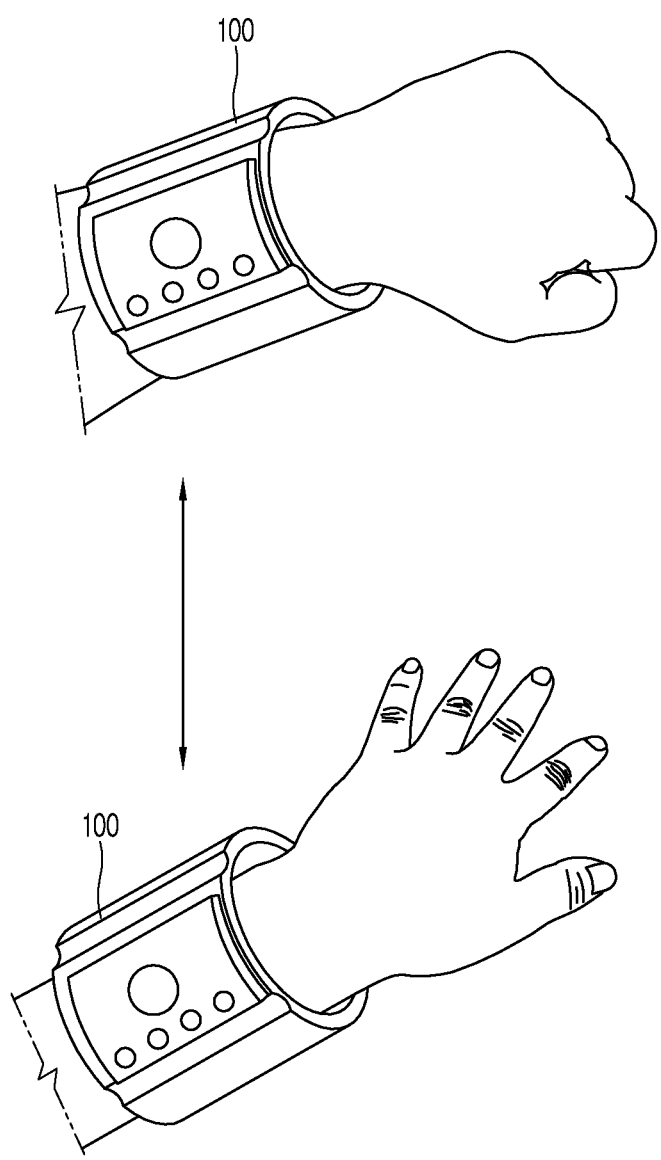
FIG. 15 is a conceptual view illustrating the control method of FIG. 14 in the terminal according to an embodiment of the present invention.

FIG. 14 is a flow chart illustrating a control method for controlling a control signal in the terminal according to an embodiment of the present invention. FIG. 15 is a conceptual view illustrating the control method of FIG. 14 in the terminal according to an embodiment of the present invention.

First, according to a control method according to an embodiment of the present invention, the sensing unit 140 (please see FIG. 1) senses a movement of at least one of tendons passing through the user's wrist and the user's wrist (S410). Here, the sensing unit 140 is disposed in a portion in which the body of the terminal 100 meets the user's wrist. Also, the tendons as a sensing target of the sensing unit 140 are tendons included in the carpal tunnel 410 discussed above with reference to (b) of FIG. 2C.

When a movement of at least one of the tendons and the user's wrist is sensed by the sensing unit 140 in step S410, the controller 180 generates a control signal for executing a function previously matched to the sensed movement characteristics of at least one of the tendons and user's wrist (S420).

Here, as discussed above, the movement characteristics of at least one of the tendons and the user's wrist may be a shape (or gesture) of the user's finger(s), a change in grasping power, a movement speed of the user's finger(s), a position of the user's wrist, a movement speed of the user's wrist, acceleration of the user's wrist, and an angular velocity of the user's wrist. Also, the movement characteristics may be variously altered according to a movement of the user's finger(s) or wrist.

For example, movement characteristics when five fingers are spread out and those when five fingers are cupped are different. Namely, movements and shapes of the tendons differ according to movements of the fingers. Also, when the user's wrist that the terminal 100 is put on moves to a position adjacent to the user's ear in an erect posture, movement characteristics differ according to a position of the user's wrist and a movement speed of the user's wrist.

Namely, the controller 180 generates a control signal for executing different functions corresponding to different movement characteristics of the tendons. For example, when a shape (or a gesture) of a finger corresponds to a pre-set first shape, the controller 180 may generate a first control signal corresponding to a first function matched to the first shape. Also, when a shape of the finger corresponds to a pre-set second shape, the controller 180 may generate a second control signal corresponding to a second function matched to the second shape.

Also, here, the control signal for executing a 'previously matched function' is a control signal for controlling an external device. The control signal is transmitted to the external device desired to be controlled by the wireless communication unit 110. Thus, the external device may be controlled to execute a function according to the control signal generated on the basis of the movement characteristics of the tendons and the user's wrist sensed by using the terminal 100 according to an embodiment of the present invention.

Here, the external device may include mobile terminals such as a cellular phone, a smart phone, a laptop computer, a digital broadcasting terminal, a PDA (personal digital assistant), a PMP (portable multimedia player), a navigation device, a slate PC, a tablet PC, an ultra book, and the like, and fixed terminal such as a digital TV, a desktop computer, and the like. Besides terminals, the external device may include any electronic device that can be remotely controlled by a control signal, such as a refrigerator, an air-conditioner, and the like.

As described above, in the terminal 100 according to an embodiment of the present invention, by simply sensing movements of tendons or a shape according to a movement, various different functions may be executed in the terminal according to an embodiment of the present invention. Also, functions matched to movement characteristics of different fingers may be set according to a user selection or an initial setting, respectively.

For example, referring to FIG. 15, when all the user's fingers are spread out from a state in which the user clenches his fist, a control signal corresponding to a function of turning on power is generated. As a result, the external device synchronized with the terminal 100 may turn on power in response to the control signal.

Conversely, when the user makes a first in a state in which all the user's fingers are spread out, a control signal corresponding to a function of turning off power is generated. As a result, the external device synchronized with the terminal 100 may turn off power in response to the control signal.

Meanwhile, besides the example discussed above with reference to FIG. 15, the controller 180 may be able to execute a pre-set function on the basis of a dynamic movement and a movement speed of the user's finger(s), a change in grip, or a movement and a speed of the user's wrist.

As described above, in the terminal 100 according to an embodiment of the present invention, different functions may be executed according to different finger gestures. Thus, the user may execute a desired function only through a movement of his finger(s) or wrist, without having to apply a control command through a touch to the external device.

FIGS. 16A through 16D are conceptual views illustrating a method for generating various control signals according to different motion characteristics in the terminal according to an embodiment of the present invention.

Figure 16A:
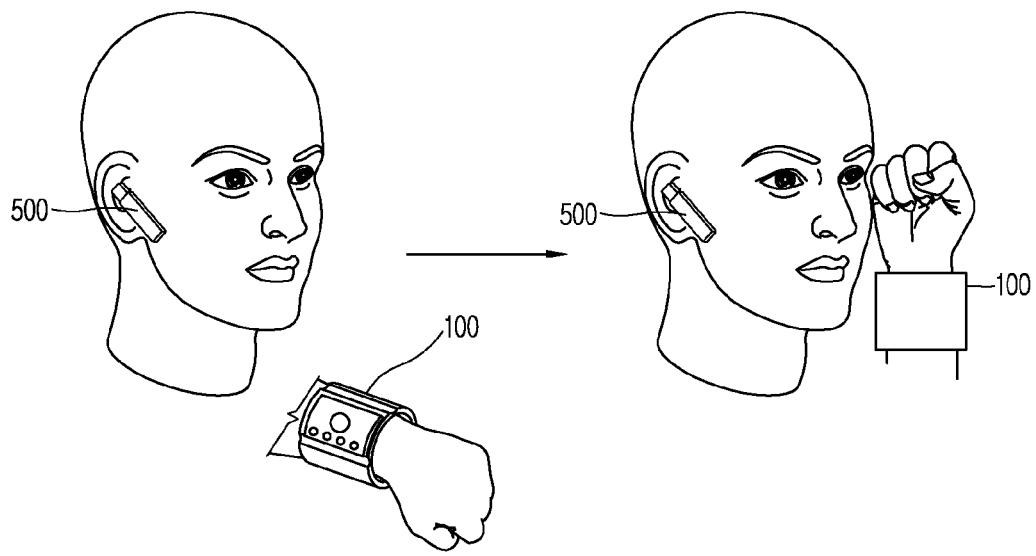
FIGS. 16A through 16D are conceptual views illustrating a method for generating various control signals according to different motion characteristics in the terminal according to an embodiment of the present invention.
Figure 16B:
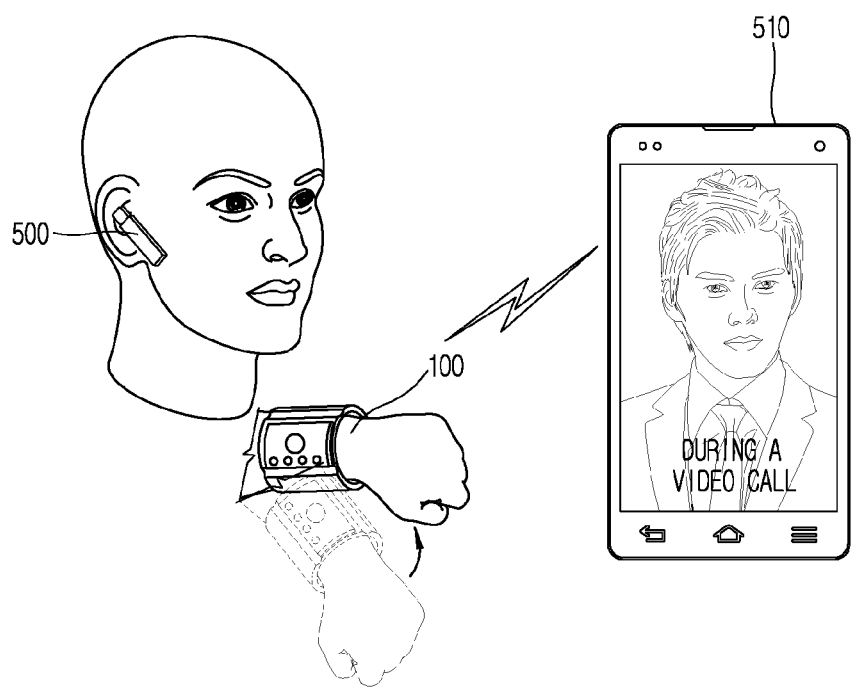
Figure 16C:
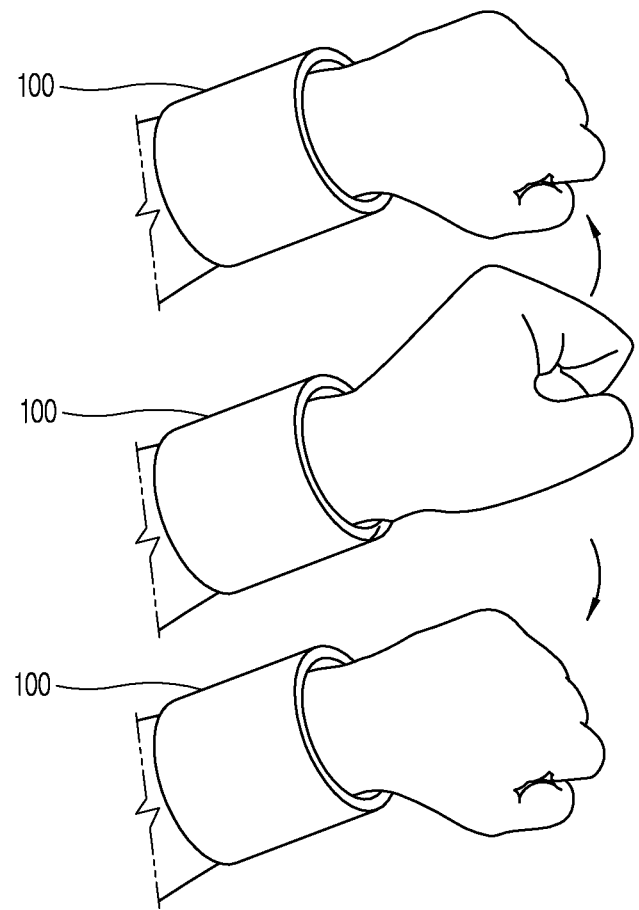

For example, in FIGS. 16A through 16C, it is assumed that a call is received and an incoming call sound is output to a Bluetooth earphone 500. The Bluetooth earphone may be replaced by a wired headset or a speaker having a mouse.

Here, the sensing unit 140 may sense movement characteristics of the user's wrist, to which it is attached, moving. In such a case, the controller 180 may generate a control signal on the basis of the movement of the user's wrist and a position to which the user's wrist has moved to place.

For example, referring to FIG. 16A, when the user's wrist moves to a position adjacent to the user's ear, the terminal 100 may generate a control signal for connecting a call. The controller 180 may transmit the control signal for connecting a call to the Bluetooth earphone 500. Accordingly, the user may perform call communication by using the Bluetooth earphone 500.

In another example, referring to FIG. 16B, when the user's wrist moves to a position adjacent to the heart, the terminal may generate a control signal for outputting information regarding the received call to the display unit. The controller 180 may output the information regarding the received call to the display unit provided in the body of the terminal 100 or transmit a control signal for enabling the external device 510 positioned nearby to output the information.

In another example, referring to FIG. 16C, in a case in which the user repeatedly moves his wrist left and right, the terminal 100 my refuse to receive a call and transmit a pre-set text message such as 'in a meeting' to a caller terminal.

Figure 16D:
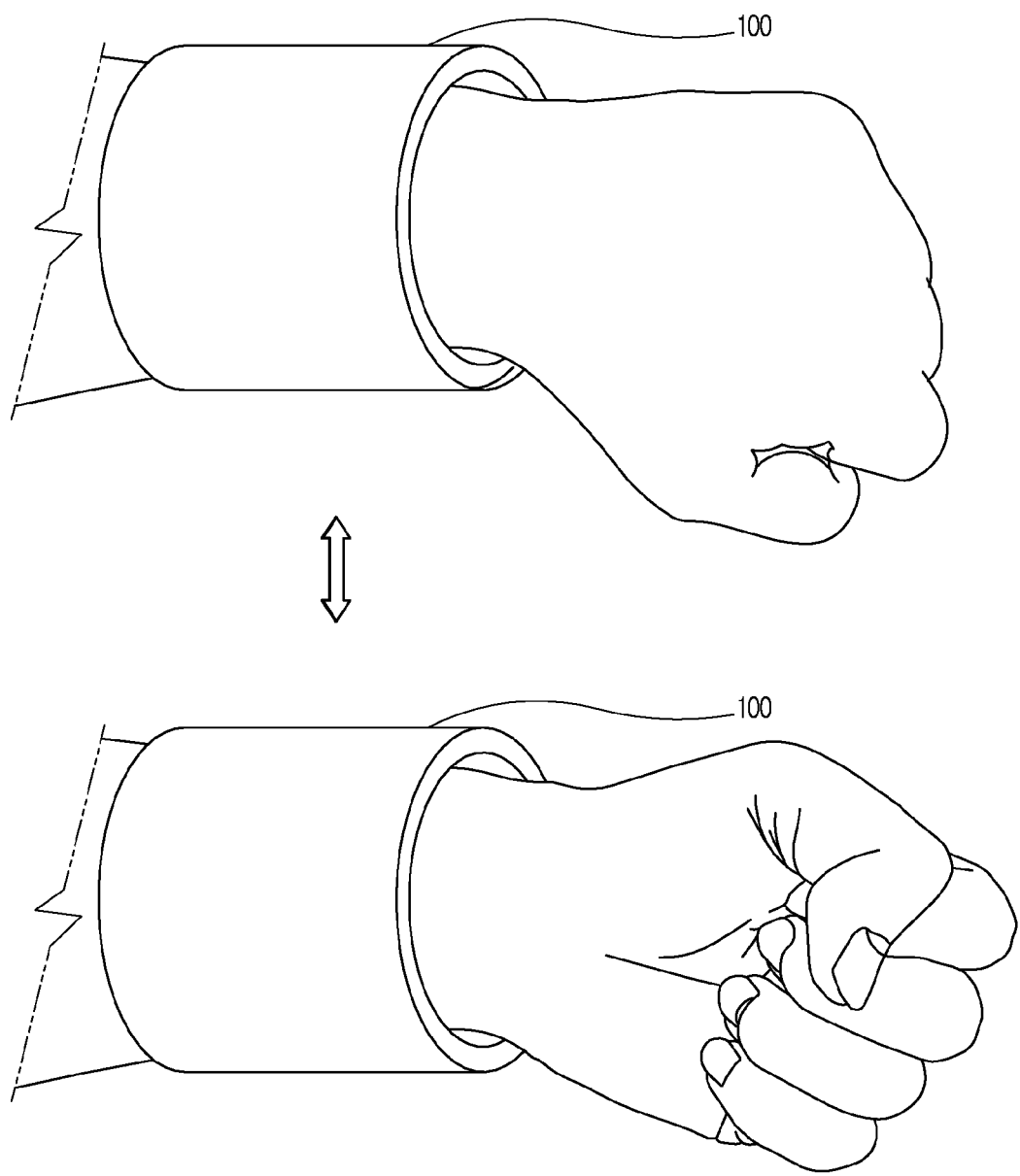

Also, the terminal 100 may control various functions according to a direction in which the user's wrist faces. Referring to FIG. 16D, the controller 180 may generate a control signal for performing the opposite functions according to a direction in which the user's wrist faces.

For example, in a state in which a volume change mode is executed, when the back of the user's hand faces the sky, the controller 180 may generate a control signal for turning up the volume, and when the back of the user's hand faces the ground, the controller 180 may generate a control signal for turning down the volume. Besides, the controller 180 may generate a control signal for outputting a next page (contents, a channel, etc) or a previous page (contents, a channel, etc.).

As described above with reference to FIGS. 6A through 6D, when a distance between the user's fingers is estimated, the controller 180 may generate a control signal on the basis of the information regarding the estimated distance between the user's fingers.

Here, the controller 180 may adjust a magnification of a video or an image output to a display unit of the external device on the basis of a distance between the different fingers. Namely, the controller 180 may control a zoom-in or zoom-out function on the basis of a distance between the different fingers.

For example, when an estimated distance between first and second fingers is smaller than a reference distance, the controller 180 may execute the zoom-out function. Also, when the estimated distance between the first and second fingers is greater than the reference distance, the controller 180 may execute the zoom-in function. Also, when the zoom-in or zoom-out function is executed, the controller 180 may control magnifications thereof differently according to the distance between the fingers.

Based on the same principle, a magnification of a camera provided in the external device may be adjusted or the volume of a speaker thereof may be adjusted. In this manner, according to an embodiment of the present invention, various control functions can be executed only by simple gestures using the user's wrist.

Figure 17:
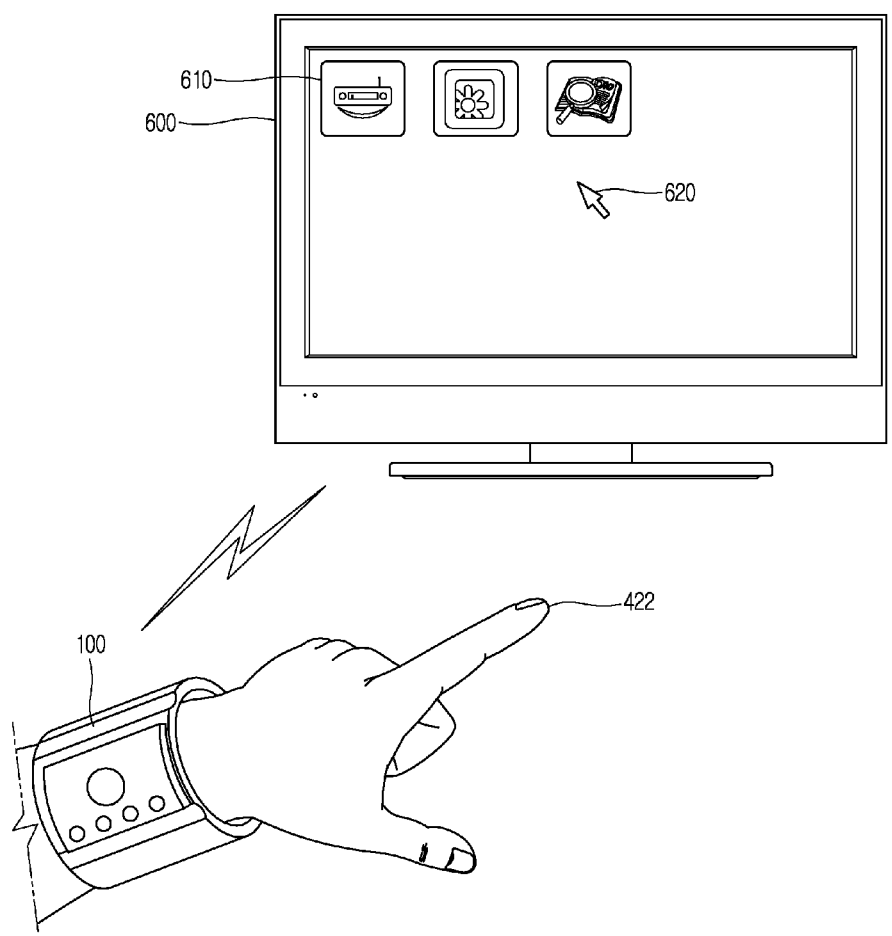
FIG. 17 is a conceptual view illustrating a method for generating a control signal for performing a mouse function in the terminal according to an embodiment of the present invention.

FIG. 17 is a conceptual view illustrating a method for generating a control signal for performing a mouse function in the terminal according to an embodiment of the present invention.

A method for selecting at least one of selection target items displayed on a display unit 600 of an external device, on the basis of movement characteristics of tendons will be described. Referring to FIG. 17, the controller 180 may move a graphic object (or a touch pointer) 620 displayed on the display unit 600 of the external device. The controller 180 may also be able to move a graphic object according to a movement of the user's wrist, rather than the user's finger 422.

In a state in which the graphic object (or the touch pointer) 620 has been moved onto an icon 610, when the user makes a fist, the controller 180 may generate a control signal for executing a function such as a click of a mouse. Namely, an application corresponding to the icon 610 may be executed.

Also, the controller 180 may generate different control signals according to grasping power of the user's fist. For example, when grasping power stronger than reference grasping power is sensed, the controller 180 may generate a control signal for executing a function corresponding to a drag, rather than a click of a mouse. Namely, in a state in which the graphic object (or the touch pointer) 620 has been moved onto the icon 610, when grasping power stronger than the reference grasping power is sensed, the position of the icon 610 may also be moved according to a movement of the user's wrist.

Hereinafter, a method for executing a function corresponding to a movement of the user's finger(s) or wrist only when a starting gesture is sensed will be described in detail with reference to the accompanying drawings. FIG. 18 is a conceptual view illustrating a method for receiving a preparatory movement in the terminal according to an embodiment of the present invention.

In the terminal 100 according to an embodiment of the present invention, in a case in which the user simply moves his finger(s) or hand, rather than intentionally moving it to generate a control signal, an erroneous generation of a control signal in response thereto is prevented. Namely, in the terminal 100 according to an embodiment of the present invention, only when a pre-set starting gesture is sensed, the controller 180 may generate a control signal corresponding to movement characteristics of tendons sensed by the sensing unit 140.

Here, the pre-set starting gesture may be based on a user setting or may correspond to initial setting information.

For example, in a case in which the pre-set starting gesture is a gesture of moving the second finger 422 in a certain direction once and the second finger 422 moves to correspond to the pre-set starting gesture, the controller 180 may generate a control signal related to a function corresponding to the movement characteristics of the tendons, after the starting gesture is sensed.

Also, in order to inform the user that the starting gesture has been sensed, as illustrated in FIG. 18, the controller 180 may output guidance information by using an output unit 150'. Also, the guidance information may be output through an auditory or tactile method such as a voice, vibration, and the like, in addition to the visual method illustrated in FIG. 18.

Also, after the starting gesture was sensed, in a case in which a pre-set period of time has lapsed or in a case in which a pre-set finish gesture is sensed, although movements of tendons are sensed by the sensing unit 140, the controller 180 may not execute a function corresponding to the sensed movements of the tendons.

As described above, in the terminal according to an embodiment of the present invention, only when a starting gesture is sensed, a function corresponding to movement characteristics of tendons is executed, whereby execution of an unnecessary function not intended by the user can be prevented.

Figure 19:
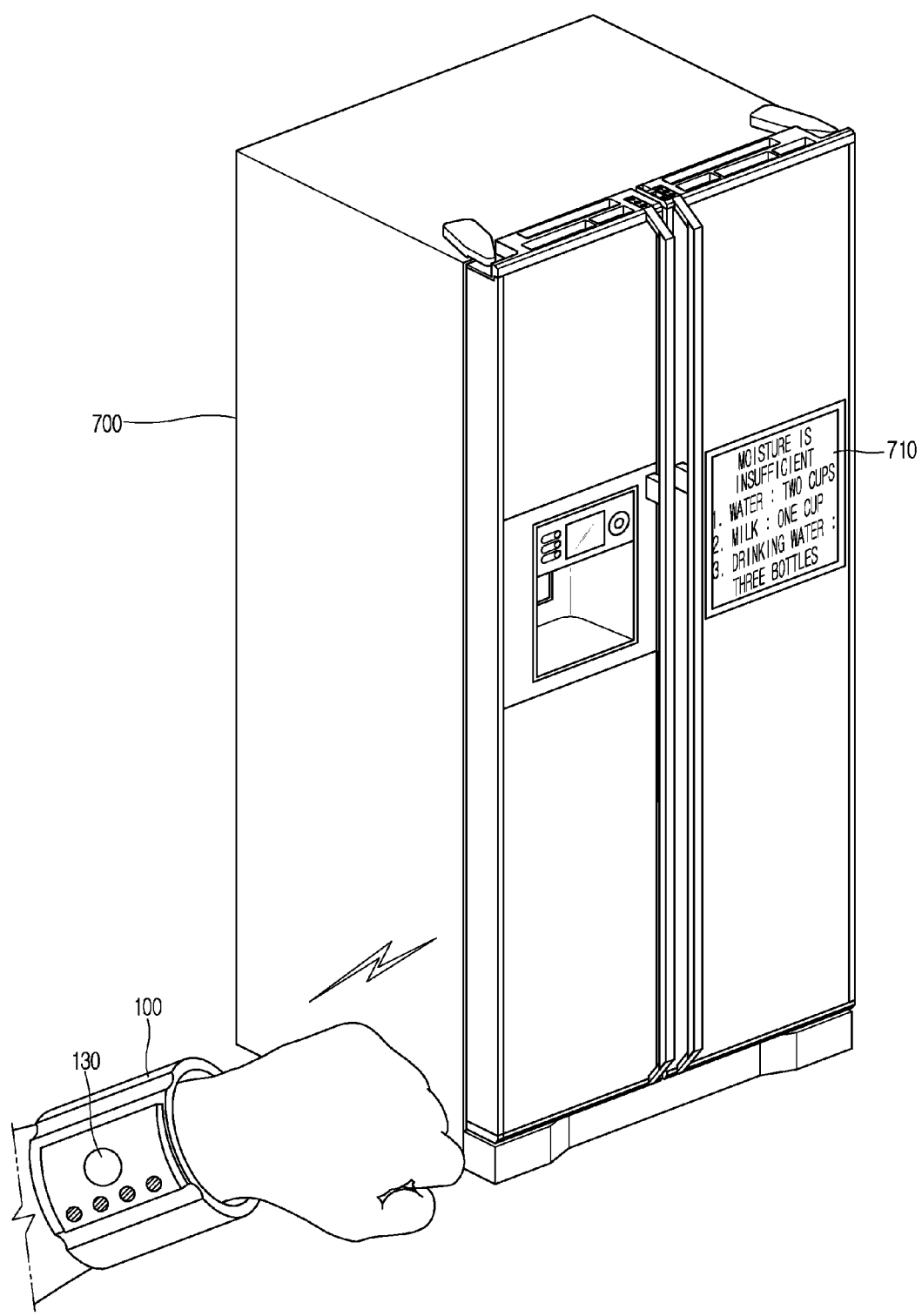
FIG. 19 is a conceptual view illustrating a method for generating a control signal by using motion characteristics of a user's wrist, and the like, and a bio-signal in the terminal according to an embodiment of the present invention.

FIG. 19 is a conceptual view illustrating a method for generating a control signal by using motion characteristics of a user's wrist, and the like, and a bio-signal in the terminal according to an embodiment of the present invention.

The terminal 100 may generate a control signal by using a bio-signal measurable from the user's wrist, as well as movement characteristics of at least one of tendons and the user's wrist.

In particular, the bio-signal sensing unit 144 (please see FIG. 10) may sense at least one bio-signal among ECG, PPG, EMG, GSR, a heat dissipation amount, a body temperature, a blood pressure, and breath.

The controller 180 may determine a body condition of the user by using the bio-signal sensed by the bio-signal sensing unit 144 and generate a control signal according to the determined body condition.

For example, it may be determined that the user is asleep. Here, if an external device is a part of a vehicle according to the results of searching for a peripheral external device, the controller 180 may generate a control signal for outputting a warning signal to prevent the user from drowsy driving. Alternatively, when the external device is a television or a radio set, the controller 180 may generate a control signal for turning off power of the external device to save electricity.

In another example, referring to FIG. 19, the terminal 100 may determine that a body condition of the user requires moisture absorption by using the sensed bio-signal. Here, the controller 180 may generate a control signal for outputting information regarding moisture absorption to a refrigerator 700. Also, the controller 180 may transmit a sensed bio-signal together with the control signal to the refrigerator 700. Upon receiving the control signal and the bio-signal, the refrigerator 700 may analyze food items provided in the refrigerator 700, select the most appropriate food on the basis of the bio-signal, and output information regarding the selected food to a display unit 710.

As described above, in the terminal according to an embodiment of the present invention, as well as executing a function of an external device through a gesture according to a movement of a user, an external device can be controlled to provide optimal information on the basis of the bio-signal of the user. Thus, the terminal and the control method thereof according to embodiments of the present invention can provide a novel interface and increase user convenience.

In the embodiments of the present invention, the foregoing method may be implemented as codes that can be read by a processor in a program-recorded medium. The processor-readable medium may include any types of recording devices in which data that can be read by a computer system is stored. The processor-readable medium may include a ROM, a RAM, a CD-ROM, a magnetic tape, a floppy disk, an optical data storage device, and the like. The processor-readable medium also includes implementations in the form of carrier waves or signals (e.g., transmission via the Internet).

The terminal according to the embodiments of the present disclosure is not limited in its application of the configurations and methods, but the entirety or a portion of the embodiments can be selectively combined to be configured into various modifications.

As the exemplary embodiments may be implemented in several forms without departing from the characteristics thereof, it should also be understood that the above-described embodiments are not limited by any of the details of the foregoing description, unless otherwise specified, but rather should be construed broadly within its scope as defined in the appended claims. Therefore, various changes and modifications that fall within the scope of the claims, or equivalents of such scope are therefore intended to be embraced by the appended claims.

What is claimed is:

1. A terminal comprising:
    a body configured to detachably wrap around a user's wrist;
    a flexible display unit that is bowable and positioned on a first region of the body;
    a sensing unit positioned on a surface of the body and configured to sense a direction in which the user's wrist faces and to sense movements of tendons passing through the wrist, the movements caused by movements of the user's fingers;
    a first camera and a second camera located at different positions of the body and facing in different directions; and
    a controller configured to:
        select at least the first camera or the second camera based on the sensed direction;
        cause the flexible display unit to display an image received from the selected camera, the image displayed on a region of the flexible display unit based on the sensed direction;
        execute a first function related to the image when a shape formed by the sensed movements matches any of a plurality of predetermined shapes;
        determine a position where the display unit wraps around the wrist by determining an area where the sensing unit and the wrist are in contact with each other;
        control a size of a specific display region of the display unit based on the determined position; and
        adjust a sensitivity of the sensing unit based on the determined position.

2. The terminal of claim 1, wherein at least the plurality of predetermined shapes or the first function is set by the user.

3. The terminal of claim 1, wherein the controller is further configured to control a zoom function of the first camera and the second camera according to a distance between two of the user's fingers.

4. The terminal of claim 1, wherein:
    the body comprises a camera sensor configured to sense a direction of the user's eyes; and
    the controller is further configured to control a specific display region of the display unit based on the sensed direction.

5. The terminal of claim 4, wherein:
    the sensing unit is further configured to sense movement of the user's wrist; and
    the controller is further configured to control the specific display region based on the sensed movement of the user's wrist.

6. The terminal of claim 1, wherein the controller is further configured to:
    cause the display unit to display one or more selection target items on a specific display region; and
    select one of the one or more selection target items based on the sensed movements of the tendons corresponding to movement of one of the user's fingers.

7. The terminal of claim 1, wherein the controller is further configured to cause the display unit to:
    display a graphic object at a first position; and
    move the displayed graphic object to a second position based on movement of one of the user's fingers.

8. The terminal of claim 1, wherein the controller is further configured to cause the display unit to:
    display one or more selection target items on a specific display region; and
    select one of the one or more target items based on the sensed movements of the tendons corresponding to two or more of the user's fingers contacting each other.

9. The terminal of claim 1, further comprising:
    a wireless communication unit configured to transmit a control signal to an external device, the control signal based on the sensed movements of the tendons.

10. The terminal of claim 9, wherein the wireless communication unit is further configured to transmit the control signal only after a predetermined starting gesture is sensed by the sensing unit.

11. The terminal of claim 9, wherein:
    the sensing unit comprises:
        a physical signal sensing unit configured to sense the movements of the tendons; and a bio-signal sensing unit configured to sense a measurable bio-signal from the user's wrist; and the controller is further configured to generate the control signal based on at least the sensed movements of the tendons and the sensed bio-signal.

12. The terminal of claim 11, wherein the wireless communication unit is further configured to transmit the bio-signal to the external device together with the control signal.

* * * * *